United States Patent
Tseng et al.

(10) Patent No.: US 7,979,116 B2
(45) Date of Patent: Jul. 12, 2011

(54) BODY COMPOSITION MEASURING INSTRUMENT FOR RECOGNIZING CHANGES IN BODY COMPOSITION

(75) Inventors: Feilang Tseng, Kyoto (JP); Tetsuya Sato, Nishinomiya (JP)

(73) Assignee: Omron Healthcare Co., Ltd., Kyoto (JP)

( * ) Notice: Subject to any disclaimer, the term of this patent is extended or adjusted under 35 U.S.C. 154(b) by 391 days.

(21) Appl. No.: 12/281,955

(22) PCT Filed: Jan. 26, 2007

(86) PCT No.: PCT/JP2007/051269
§ 371 (c)(1),
(2), (4) Date: Oct. 1, 2008

(87) PCT Pub. No.: WO2007/108229
PCT Pub. Date: Sep. 27, 2007

(65) Prior Publication Data
US 2009/0204018 A1   Aug. 13, 2009

(30) Foreign Application Priority Data

Mar. 17, 2006 (JP) .................. 2006-074495

(51) Int. Cl.
*A61B 10/00* (2006.01)
*A61B 5/103* (2006.01)
*A61B 5/117* (2006.01)
*G01G 9/00* (2006.01)
*G01G 17/00* (2006.01)
*G01G 19/00* (2006.01)
*G01G 23/38* (2006.01)
*G01G 19/40* (2006.01)
*G01G 23/18* (2006.01)
*G01B 5/26* (2006.01)
*G01B 11/28* (2006.01)
*G01B 21/10* (2006.01)

(52) U.S. Cl. ................ 600/547; 600/587; 177/1; 177/2; 177/3; 177/4; 177/5; 177/25.11; 177/25.12; 177/25.13; 702/156; 702/157; 702/173

(58) Field of Classification Search .................. 600/547, 600/587; 177/1–5, 25.11–25.14, 25.19; 702/156–157, 173

See application file for complete search history.

(56) References Cited

U.S. PATENT DOCUMENTS
4,689,615 A * 8/1987 Del Rosso ................. 345/440.2
(Continued)

FOREIGN PATENT DOCUMENTS
EP   1 576 923   9/2005
(Continued)

OTHER PUBLICATIONS

Russian Office Action dated Oct. 8, 2009, directed to corresponding Russian Patent Application No. 2008141147/(053293); 6 pages.
(Continued)

*Primary Examiner* — Max Hindenburg
*Assistant Examiner* — Sean P Dougherty
(74) *Attorney, Agent, or Firm* — Morrison & Foerster LLP

(57) ABSTRACT

A body composition measuring instrument includes a body composition calculating unit for calculating the body composition of a user by using a plurality of electrodes, a reference value storage region for storing information of a reference value related to the past body composition of the user, a display control unit for performing a control to display a position of the body composition during the time calculated by the body composition calculating unit in reference to a line showing the reference value on a predetermined graph, and a display section for providing a display corresponding to the output from the display control unit.

13 Claims, 18 Drawing Sheets

U.S. PATENT DOCUMENTS

| | | | | |
|---|---|---|---|---|
| 5,582,186 A * | 12/1996 | Wiegand | | 600/595 |
| 5,817,031 A * | 10/1998 | Masuo et al. | | 600/547 |
| 5,989,200 A * | 11/1999 | Yoshimura et al. | | 600/587 |
| 6,354,996 B1 * | 3/2002 | Drinan et al. | | 600/300 |
| 6,734,856 B2 * | 5/2004 | Ishikawa et al. | | 345/440 |
| 6,920,352 B2 * | 7/2005 | Shimomura et al. | | 600/547 |
| 7,075,537 B2 * | 7/2006 | Simond et al. | | 345/440.2 |
| 7,252,635 B2 * | 8/2007 | Itagaki | | 600/300 |
| 7,336,992 B2 * | 2/2008 | Shiokawa | | 600/547 |
| 7,764,991 B2 * | 7/2010 | Yamazaki et al. | | 600/547 |
| 2001/0011043 A1 * | 8/2001 | Ishikawa et al. | | 473/316 |
| 2001/0053883 A1 * | 12/2001 | Yoshimura et al. | | 600/587 |
| 2002/0052697 A1 * | 5/2002 | Serita | | 702/30 |
| 2004/0064071 A1 * | 4/2004 | Kasahara | | 600/595 |
| 2004/0220492 A1 * | 11/2004 | Kodama et al. | | 600/547 |
| 2005/0124865 A1 * | 6/2005 | Kawanishi | | 600/300 |
| 2007/0038140 A1 * | 2/2007 | Masuo et al. | | 600/547 |

FOREIGN PATENT DOCUMENTS

| | | |
|---|---|---|
| JP | 63-293423 | 11/1988 |
| JP | 11-76187 | 3/1999 |
| JP | 2002-45346 | 2/2002 |
| JP | 2002-238870 | 8/2002 |
| JP | 2004-41811 | 2/2004 |
| JP | 2004-180939 | 7/2004 |
| JP | 2005-218582 | 8/2005 |
| JP | 2005-261488 | 9/2005 |

OTHER PUBLICATIONS

International Search Report directed to PCT/JP2007/051269.

International Preliminary Report on Patentability directed to PCT/JP2007/051269.

* cited by examiner

Fig. 5
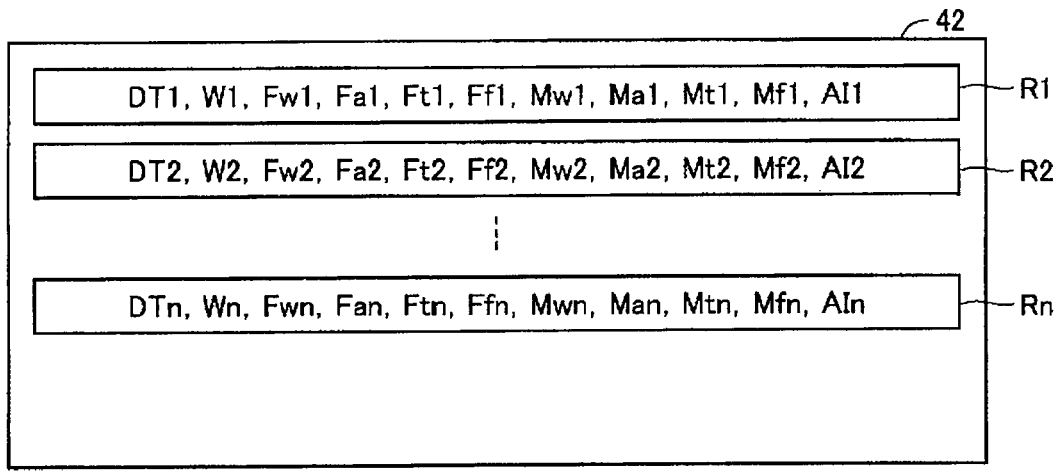
Fig. 6
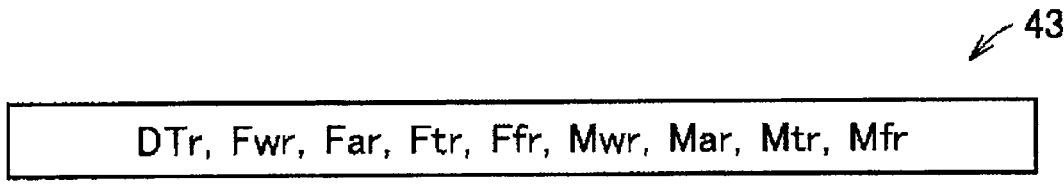
Fig. 7A
| Range of body fat percentage | Display width with respect to a reference point |
|---|---|
| Less than 10% | ±2.0% |
| Greater than or equal to 10% to less than 25% | ±3.0% |
| Greater than or equal to 25% | ±4.0% |
Fig. 7B
| Range of muscle percentage | Display width with respect to a reference point |
|---|---|
| Entire range | ±2.0% |

BODY COMPOSITION MEASURING INSTRUMENT FOR RECOGNIZING CHANGES IN BODY COMPOSITION

REFERENCE TO RELATED APPLICATIONS

This application is a national stage application under 35 USC 371 of International Application No. PCT/JP2007/051269, filed Jan. 26, 2007, which claims the priority of Japanese Patent Application No. 2006-074495, filed Mar. 17, 2006, the contents of both of which prior applications are incorporated herein by reference.

FIELD OF THE INVENTION

The present invention relates to a body composition measuring instrument, in particular, to a body composition measuring instrument for calculating composition component of a body through a bioelectric impedance method.

BACKGROUND OF THE INVENTION

In a conventional body composition measuring instrument, the measurement result of the composition component of the body (hereinafter referred to as "body composition") is displayed in various modes. For instance, Japanese Laid-Open Patent Publication No. 11-76187 (hereinafter referred to as patent document 1) has described bar displaying the extent of measurement results of the body fat percentage in a total of twelve levels by using expressions like slim, standard, slightly obese, and obese. Japanese Laid-Open Patent Publication No. 2002-238870 (hereinafter referred to as patent document 2) has disclosed bar displaying the extent of measurement result of visceral fat area over three areas of standard, slightly excess, and excess.

Proposal also has been made in displaying the comparison result with a measurement value in a different opportunity or a measurement value of a different type so to be easily understood by the user. For instance, Japanese Laid-Open Patent Publication No. 2004-180939 (hereinafter referred to as patent document 3) has disclosed comparing a measurement result with an average value, and bar displaying or displaying in radar chart such result. This document has also disclosed displaying in numerical value, or displaying in sound, voice, or color the comparison result with the preset target value. Japanese Laid-Open Patent Publication No. 2004-41811 (hereinafter referred to as patent document 4) has disclosed comparing the measurement results of body fat, visceral fat, and basal metabolism with past values, and displaying the tendency of increase/decrease with the direction of the arrow.

Japanese Laid-Open Patent Publication No. 2005-261488 (hereinafter referred to as patent document 5) has disclosed comparing increase/decrease in muscle percentage and increase/decrease in body fat percentage, and changing the background color of the LCD between good tendency (decrease of body fat is large and decrease of muscle is small compared thereto) and bad tendency.

SUMMARY OF THE INVENTION

However, such conventional body composition measuring instruments have the following problems. When displaying the comparison result with the average value as in patent documents 1 to 3, the comparing target for determining the extent of the measurement value is the user of the entire database, and the past measurement value and the current measurement value of the user himself/herself cannot be compared and displayed. Furthermore, although comparison with the past measurement value of the user himself/herself can be made as in patent document 4, the extent of change is hard to understand as it is displayed by the direction of the arrow.

In patent document 5, the tendency in change is displayed in color and thus is easy to see, but the tendency in change with respect to the target value or the midterm progress of an ideal weight loss is hard to understand.

In view of the above problems, it is an object of the present invention to provide a body composition measuring instrument capable of displaying change in body composition of the user himself/herself in an easily understandable manner.

It is another object of the present invention to provide a body composition measuring instrument capable of displaying whether the tendency in change of the body composition of the user himself/herself is a good tendency or a bad tendency with respect to the target value or the ideal midterm progress in a mode easily understandable by the user.

A body composition measuring instrument according to one aspect of the present invention includes a plurality of electrodes to be contacted to a surface of a body of a user; a first calculating unit for calculating a body composition of the user by using the electrodes; a storage section for storing information of a reference value related to past body composition of the user; a display control unit for performing a control to display a position of a body composition for this time and a position of the reference value calculated by the first calculating unit on a predetermined graph; and a display section for performing a display corresponding to an output from the display control unit; wherein the position of the reference value is a predetermined fixed position in the predetermined graph; the reference value corresponds to a body composition calculated by the first calculating unit at a specific time point in the past; the display control unit includes a first determining unit (122) for determining a display mode of a component in the predetermined graph corresponding to the body composition for this time based on the body composition for this time and the reference value, and a second determining unit (122) for determining a range of values of the body composition displayable on the predetermined graph based on the reference value; and the first determining unit determines the display mode based on the range determined by the second determining unit.

The term "body composition" desirably includes at least one of body fat percentage, muscle percentage, fat free mass, body fat mass, muscle mass, visceral fat level, basal metabolism, BMI, and age index (index representing what average value of which age the basal metabolism corresponds to).

The position of the reference value is preferably a predetermined fixed position in a predetermined graph.

The predetermined graph preferably includes a first block group and a second block group respectively arranged before and after the position of the reference value.

The number of blocks included in the first block group is preferably greater than number of blocks included in the second block group.

An operating section for accepting an instruction from the user, and a storage processing unit for performing a process of storing the information of the reference value in the storage section are further preferably provided, wherein the storage processing unit includes a first updating unit for updating the reference value when a predetermined instruction is input from the user.

The first updating unit preferably updates the reference value to the body composition for this time when the predetermined instruction is input in a measurement of the body composition for this time.

Preferably, a timer for timing date and time is further provided, wherein the body composition calculated by the first calculating unit is stored in correspondence to a measurement date and time for every measurement in the storage section; a second calculating unit for calculating an average value of the body composition corresponded to the measurement date and time within a predetermined first period and the body composition for this time in the storage section is further provided; the storage processing unit includes a determining unit for determining whether or not the information of the reference value is stored in the storage section, and a setting unit for setting the average value as the reference value when determined that the information of the reference value is not stored in the storage section and the body composition for the first period is stored in the storage section.

The display control unit further preferably displays the position of the average value on the predetermined graph.

The information of the reference value preferably includes information on a set date of the reference value; and a notifying section for notifying to update the reference value when a predetermined second period has elapsed from the set date is further provided.

The storage processing unit further preferably includes a second updating unit for updating the reference value to the body composition for this time when the body composition for this time reaches an upper limit or a lower limit of a range displayable on a predetermined graph.

A notifying section for notifying to update the reference value in a case where the body composition for this time approaches an upper limit or a lower limit of a range displayable on a predetermined graph is preferably provided.

The display control unit further preferably displays a comparison result of the body composition for this time and a predetermined standard value in an attribute of the user near a predetermined graph.

A target value storage section for storing a target value input by the user is further preferably provided, wherein the display control unit includes a selecting unit for selecting one of a first mark and a second mark predefined based on whether or not the body composition for this time has approached that target value than before, and the mark selected by the selecting unit is further displayed with a predetermined graph.

The display control unit preferably includes a selecting unit for selecting one of a first mark and a second mark predefined based on whether or not the body composition for this time has changed in a desired tendency than before, and the mark selected by the selecting unit is further displayed with a predetermined graph.

According to the present invention, the user can intuitively recognize how much the body composition for this time has changed from the reference value.

Furthermore, the user can easily recognize that the measurement value of the body composition is changing in a good tendency or is changing in a bad tendency with respect to the target value or the ideal midterm progress.

BRIEF DESCRIPTION OF THE DRAWINGS

FIG. 5 is a view showing one example of a data structure of a measurement result storage region.

FIG. 6 is a view showing one example of a data structure of a reference value storage region.

FIG. 7A is a view showing a content example of a body fat percentage table.

FIG. 7B is a view showing a content example of a muscle percentage table.

DETAILED DESCRIPTION OF THE INVENTION

Figure 1:
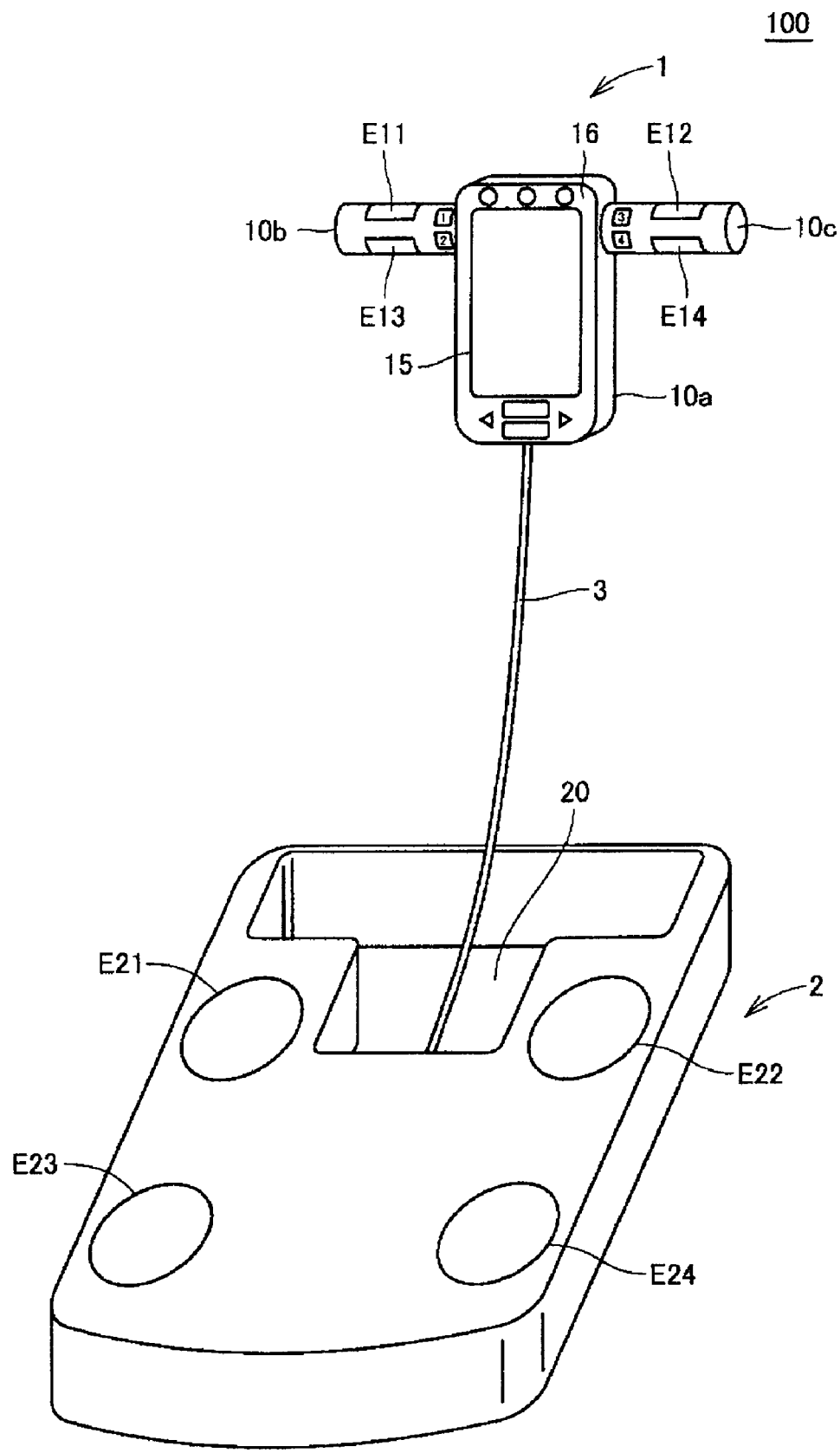
FIG. 1 is a view showing one example of an outer appearance of a body composition measuring instrument according to each embodiment of the present invention.

Embodiments of the present invention will be described in detail with reference to the drawings. Same reference numerals are denoted for the same or corresponding portions throughout the drawings.

First Embodiment

Outer Appearance and Configuration of Body Composition Measuring Instrument According to First Embodiment of the Present Invention With reference to FIG. 1, a body composition measuring instrument 100 includes an upper limb unit 1 that can be gripped by the user with both hands, a lower limb unit 2 on which both feet of the user can be placed, and a cable 3 for electrically connecting the upper limb unit 1 and the lower limb unit 2.

The upper limb unit 1 includes a body 10a and grips 10b, 10c arranged on the left and the right of the body 10a. The body 10a is provided with a display section 15 for displaying measurement results and various information, and an operating section 16 operated by the user to accept instructions from the user and input of various information. A plurality of electrodes E11, E12, E13, and E14 is provided on the grips 10b, 10c. The grips 10b, 10c are configured so as to be gripped by the user with both hands. The electrodes E11, E13 are provided on the grip 10b for the left hand, and the electrodes E12, E14 are provided on the grip 10c for the right hand. The electrodes E11, E12 provided on the upper side (head side of the user in the measuring pose) of the respective grips 10b, 10c are current application electrodes, and the electrodes E13, E14 provided on the lower side of the respective grips 10b, 10c are voltage detection electrodes. Here, description is made such that the upper limb unit 1 includes the grips 10b, 10c configured in a handle shape, but is not limited thereto. The user merely needs to be able to grip the upper limb unit 1 with both hands and the electrodes E11 to E14 merely need to be arranged at the portion to be gripped with both hands. That is, the electrodes E11, E13 merely need to contact the left hand of the user and the electrodes E12, E14 merely need to contact the right hand.

A plurality of electrodes E21, E22, E23, and E24 are provided on the upper surface (surface on which the user places both feet) of the lower limb unit 2. The electrodes E21, E22 provided on the front side (toe side of the user in the measuring pose) of the lower limb unit 2 are current application electrodes, and the electrodes E23, E24 provided on the back side (heel side of the user in the measuring pose) of the lower limb unit 2 are voltage detection electrodes. The lower limb unit 2 includes an accommodating section 20 for accommodating the upper limb unit 1.

In the following description, the electrodes E11 to E14 are collectively referred to as "hand electrodes E10" and the electrodes E21 to E24 are collectively referred to as "feet electrodes E20".

Figure 2:
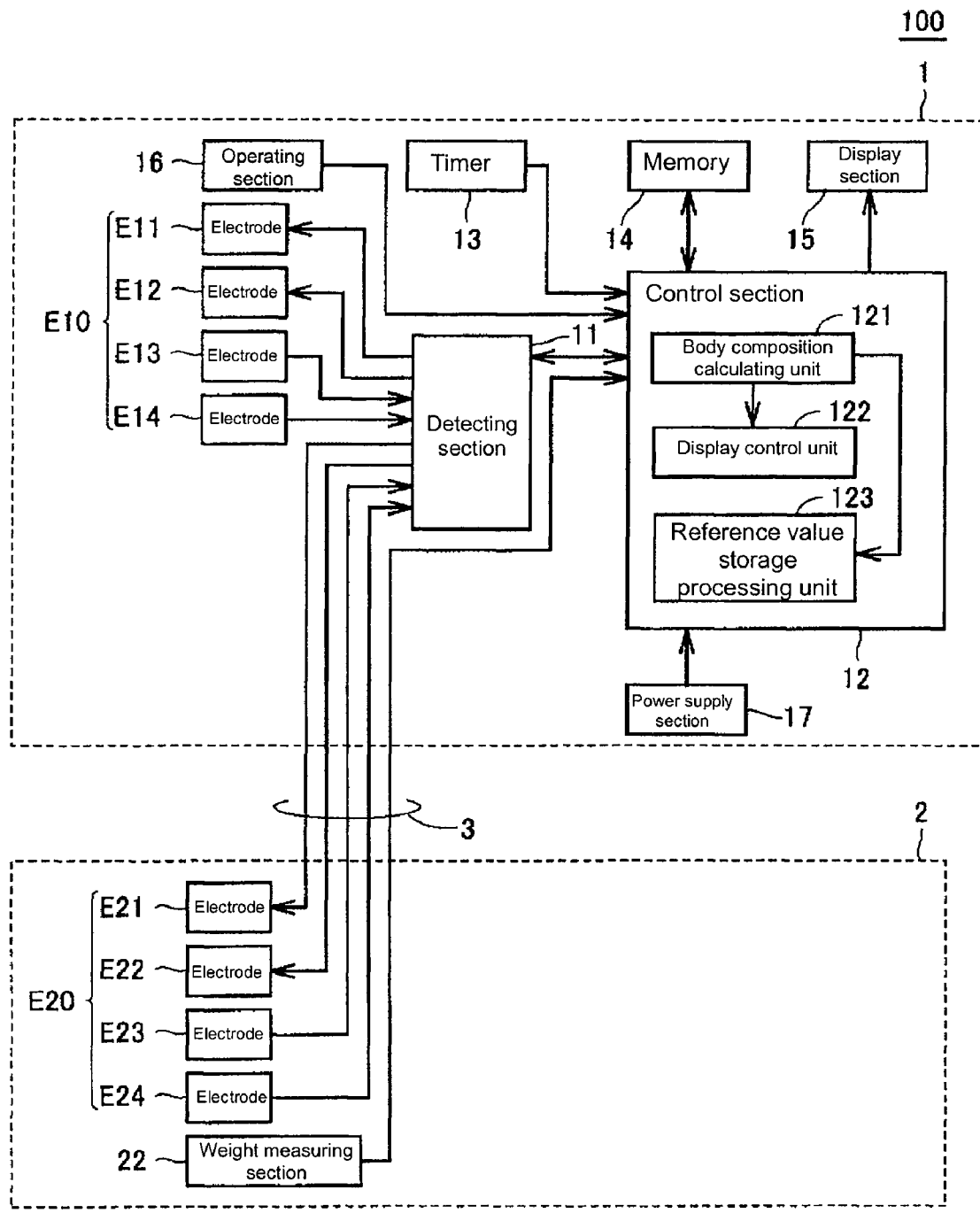
FIG. 2 is a block diagram showing a hardware configuration of the body composition measuring instrument according to each embodiment of the present invention.

FIG. 2 is a block diagram showing a hardware configuration of the body composition measuring instrument 100 according to the first embodiment of the present invention.

In addition to the hand electrodes E10, the display section 15, and the operating section 16 described above, the upper limb unit 1 further includes a detecting section 11 for detecting the potential difference between the hand and the foot (whole body) by applying current between the hands and the feet with both the hand electrodes E10 and the feet electrodes E20; a control section 12 for controlling the entire body composition measuring instrument 100; a timer 13 for measuring date and time; a memory 14 for storing various data and programs; and a power supply section 17 for supplying power to the control section 12.

The lower limb unit 2 desirably further includes a weight measuring section 22 for measuring the weight of the user, in addition to the feet electrodes E20 described above. The weight measuring section 22 is configured by a sensor, and the like.

The memory 14 is configured by a non-volatile memory such as flash memory. The configuration example of the memory 14 will be described hereinafter in detail.

The display section 15 is configured by LCD (Liquid Crystal Display) and the like.

Figure 3:
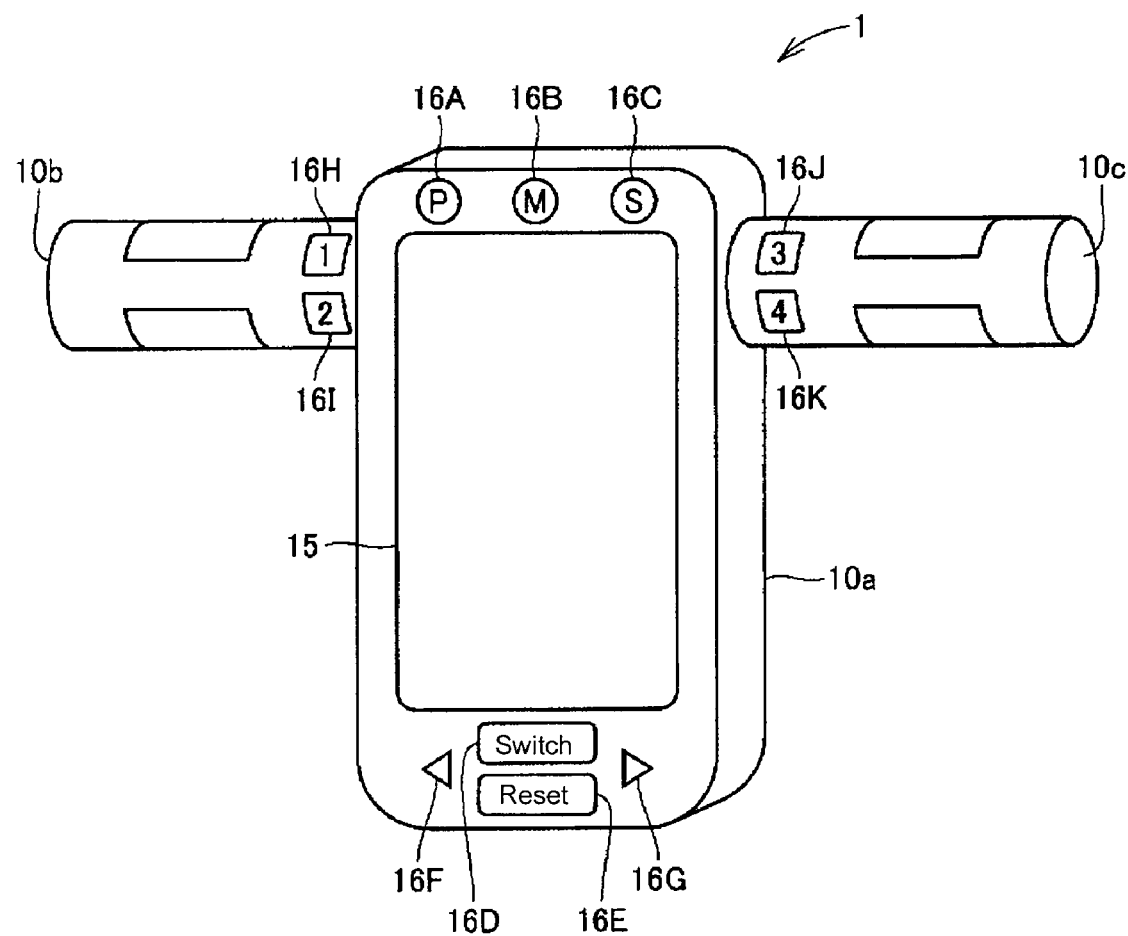
FIG. 3 is a view showing a specific example of a plurality of buttons included in an operating section.

The operating section 16 includes a plurality of buttons, and the like. FIG. 3 is a view showing a specific example of a plurality of buttons included in the operating section 16. With reference to FIG. 3, the operating section 16 includes a power button 16A for instructing ON/OFF of the power supply, a memory button 16B for instructing display of past measurement information, a measurement button 16C for instructing start of measurement, a display switch button 16D for instructing switch to other information of the information being displayed in the display section 15, a reset button 16E for instructing setting/updating of reference value to be hereinafter described, and left and right buttons 16F, 16G for moving a cursor (not shown) displayed on the display section 15 to the left and the right. The operating section 16 may include a plurality of, for example, four personal number buttons 16H, 16I, 16J, and 16K so that a plurality of users can use the body composition measuring instrument 100. In the present embodiment, description is made on the assumption that the personal number buttons 16H, 16I, 16J, 16K are included in the operating section 16.

The detecting section 11 is controlled by the control section 12 to switch the electrodes. The detecting section 11 preferably detects the potential difference between the hands or the feet by applying current to the hands or the feet of the user by either one of the hand electrodes E10 or the feet electrodes E20. The information on the detected potential difference is output to the control section 12. The detecting section 11 includes a switching switch (not shown) connected to all of the hand electrodes E10 and the feet electrodes E20, for switching the electrodes in response to the instruction from the control section 12, and a constant current generating unit (not shown) for flowing a constant current to at least one pair of current electrodes selected by the switching switch, wherein the potential difference of at least one pair of voltage electrodes selected by the switching switch is detected with a constant current being applied to the user through the current electrodes.

The control section 12 is configured by a CPU (Central Processing Unit) and the like. The control section 12 includes a body composition calculating unit 121 for calculating the body composition of the user; a display control unit 122 for performing a control to display the calculation result of the body composition calculated by the body composition calculating unit 121 on the display section 15; and a reference value storage processing unit 123 for performing a process of storing information of the reference value in a predetermined region of the memory 14.

The body composition calculating unit 121 measures a whole body impedance, a hands impedance and a feet impedance respectively based on the hands and the feet, both hands, and both feet detected by the detecting section 11. The body composition of the user is calculated based on such measured impedances.

The respective impedances are specifically measured as follows. When measuring the whole body impedance, the body composition calculating unit 121 flows current from the electrodes E11, E12 to the electrodes E21, E22, and performs a control to detect the potential difference between the electrodes E13, E14 and the electrodes E23, E24 with current being applied to the whole body of the subject. The whole body impedance is calculated (measured) based on the whole body potential difference detected in this manner. When measuring the whole body impedance, the electrode E11 and the electrode E12, the electrode E21 and the electrode E22, the electrode E13 and the electrode E14, as well as the electrode E23 and the electrode E24 are preferably short circuited. When measuring the hands impedance, the body composition calculating unit 121 flows current between the electrode E11 and the electrode E12, and performs a control to detect the potential difference between the electrode E13 and the electrode E14 with current being applied between both hands of the subject. When measuring the feet impedance, the body composition calculating unit 121 flows current between the electrode E21 and the electrode E22, and performs a control to detect the potential difference between the electrode E23 and the electrode E24 with current being applied between both feet of the subject.

In the present embodiment, the body composition calculating unit 121 calculates the body fat percentage for the whole body and for every site (e.g., arm, torso, leg), muscle percentage for the whole body and for every site, and age index based on the whole body impedance, the hands impedance, and the feet impedance.

The calculation formula of the body fat percentage (% FAT) of the whole body is expressed with the following equations (1) and (2).

$$\% \text{ FAT} = (W - FFM)/W \cdot 100 \quad (1)$$

$$FFM = a \cdot H^2/Zw + b \cdot W + c \cdot Ag + d \quad (2)$$

(wherein, FFM: fat free mass, W: weight, H: height, Zw: whole body impedance, Ag: age, a to d: constant)

The constants a to d are predefined by correlation with a reference measured with DEXA (Dual energy X-ray absorptiometry) and the like. The constants a to d may differ according to sex.

The body fat percentage for every site is calculated based on correlation with the reference measured with DEXA etc. in advance from the measured hand impedance and feet impedance, as well as the body information of the user.

The muscle percentage for the whole body and for every site can be calculated through a known method, as in the case of the body fat percentage.

The age index is calculated (selected) based on the basal metabolic mass and a predetermined age index correspondence table (not shown) stored in the memory 14. The basal metabolic mass may be calculated through a known method. The value of the basal metabolic mass, and the standard age corresponding to each value are corresponded in the age index correspondence table described above.

The display control unit 122 performs a control to display the position of the body composition for this time and the position of the reference value calculated by the body composition calculating unit 121 on the display section 15 in a predetermined graph. Thus, a graph showing the position of the body composition for this time and the position of the reference value is displayed on the display section 15.

"Reference value" corresponds to the body composition calculated by the body composition calculating unit 121 at a specific time point in the past. In a predetermined graph, the position of the reference value is preferably a predetermined fixed position. In the present embodiment, description is made on the assumption that the position of the reference value is displayed by the liquid crystal configuring the display section 15. The position of the reference value may be displayed in advance on the surface (e.g., surface of display section 15) of a housing of the body 10*a*.

In the present embodiment, the predetermined graph includes a first block group and a second block group respectively arranged on the front and the back ('−' side and '+' side) of the position of the reference value. Such graph is, for example, a bar graph. The number of blocks included in the first block group is preferably greater than the number of blocks included in the second block group. "Block" represents the minimum unit that can display the change of value in the graph, wherein the shape and size of each block, and the distance between the blocks are equal.

The display control unit 122 determines the display mode of the components in the bar graph corresponding to the body composition for this time based on the value of the body composition for this time and the reference value. That is, the display control unit 122 calculates the number of blocks to be invert displayed of the first block group and the second block group.

The display control unit 122 preferably performs a process of determining a range (hereinafter referred to as "display width") of the values of the body composition that can be displayed on the bar graph based on the reference value. The display mode of the components in the bar graph corresponding to the body composition for this time is thereby determined based on the value of the body composition for this time, the reference value, and the determined display width. A specific example of the process of determining the display width will be hereinafter described.

The reference value storage processing unit 123 sets/updates the reference value when the user pushes the reset button 16E. A specific example of the setting/updating of the reference value will be hereinafter described in detail.

The control section 12 may also calculate an average (hereinafter referred to as "weekly average value") of the value of the body composition for this time calculated by the body composition calculating unit 121, and the value of the body composition measured within a predetermined period (e.g., one week) from the present day (measurement date of the body composition for this time). In this case, the display control unit 122 specifies the position of the block corresponding to the weekly average value in the bar graph, and preferably changes the display color of the relevant block.

The control section 12 may also calculate a general evaluation in the attributes of the user. "Attribute" represents a group classified by at least one of age and sex. The calculation of the general evaluation may be specifically performed as follows. The memory 14 stores a predetermined standard value correspondence table (not shown) in which a standard value is corresponded for every attribute, and the control section 12 reads out the standard value corresponding to the attribute of the user from the standard value correspondence table. Evaluation on whether the measurement value (value of the body composition for this time) of the user is lower, higher, at standard level, etc. compared to the standard value is calculated through methods performed conventionally. In this case, the display control unit 122 preferably displays evaluation information, which is the comparison result of the measurement value of the user and the standard value, near the bar graph.

The operation of each function block shown in FIG. 2 may be realized by executing software stored in the memory 14, and at least one thereof may be realized by hardware.

A configuration example of the memory 14 will be described in detail below.

Figure 4:
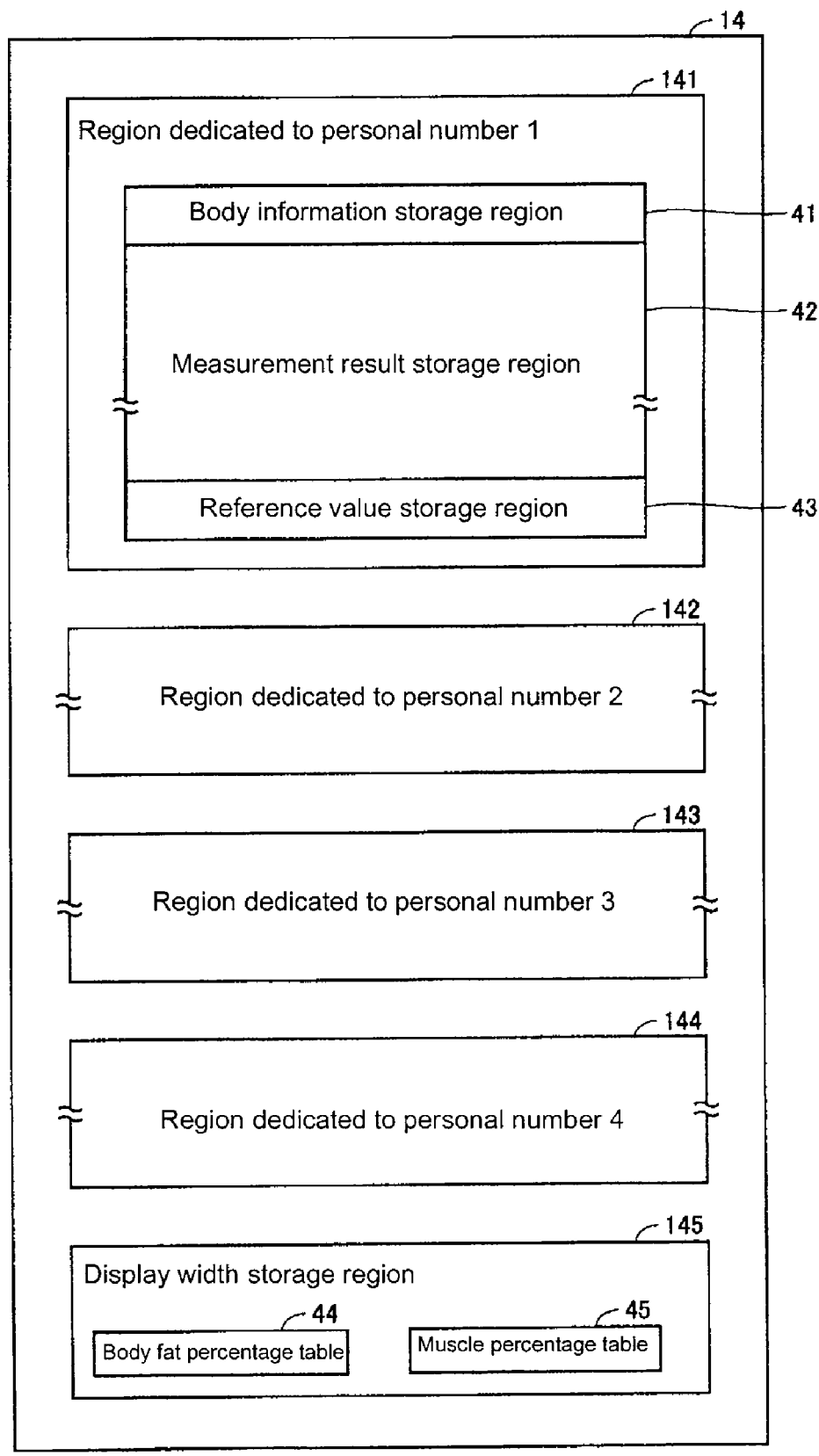
FIG. 4 is a view showing a configuration example of a memory.

With reference to FIG. 4, the memory 14 includes a region 141 for storing information about the user corresponding to a personal number 1, a region 142 for storing information about the user corresponding to a personal number 2, a region 143 for storing information about the user corresponding to a personal number 3, a region 144 for storing information about the user corresponding to a personal number 4, and a display width storage region 145.

The region 141 includes a body information storage region 41 for storing body information of the user corresponding to the personal number 1, a measurement result storage region 42 for storing the measurement result of the user corresponding to the personal number 1, and a reference value storage region 43 for storing information on the reference value of the user corresponding to the personal number 1. The regions 142 to 144 corresponding to other personal numbers also include storage regions similar to those of the region 141.

The "body information" is information necessary for calculating the body composition, and includes, age, sex, height, weight, and the like. The body composition measuring instrument 100 according to the present embodiment includes the weight measuring section 22, and thus age data, sex data, and height data based on the input from the user of the body information are stored in the body information storage region 41.

One example of a data structure of the measurement result storage region 42 is shown in FIG. 5. When a body composition measuring process described in detail hereinafter is executed, the measurement result is stored in units of records R in the measurement result storage region 42 corresponding to the personal number specified by the user. The record R (R1, R2, . . . , Rn) includes date and time data DT in body composition measurement (e.g., in potential difference detection), weight value data W serving as body information, body fat percentage data Fw of the whole body, body fat percentage data Fa of the arm, body fat percentage data Ft of the torso, body fat percentage data Ff of the leg, muscle percentage data Mw of the whole body, muscle percentage data Ma of the arm, muscle percentage data Mt of the torso, muscle percentage data Mf of the leg, and age index data AI. Such data merely need to be stored in each region in correspondence for every measurement, and it is not limited to the storage form using the record R.

One example of a data structure of the reference value storage region 43 is shown in FIG. 6. The reference value storage region 43 stores data DTr indicating the date and time (referred to as "set date") on which the reference value is set/updated, reference value data Fwr of the body fat percentage of the whole body, reference value data Far of the body fat percentage of the arm, reference value data Ftr of the body fat percentage of the torso, reference value data Ffr of the body fat percentage of the leg, reference value data Mwr of the muscle percentage of the whole body, reference value data Mar of the muscle percentage of the arm, reference value data Mtr of the muscle percentage of the torso, and reference value data Mfr of the muscle percentage of the leg.

As described above, each storage region is provided in advance for every personal number in the present embodiment. However, information on the body information, the measurement result, and the reference value of the user merely need to be stored in association with the personal number, and the storage region for every personal number may not be provided.

In the present embodiment, the reference value storage region 43 is provided to store information of the reference value, but such dedicated region may not be arranged. For instance, identification data capable of identifying which measurement result data is the data of the reference value may be contained in the measurement result storage region 42.

The display width storage region 145 includes a body fat percentage table 44 and a muscle percentage table 45 in advance. The content example of the body fat percentage table 44 and the muscle percentage table 45 is shown in FIG. 7A and FIG. 7B. FIG. 7A is a view showing a content example of the body fat percentage table 44, and FIG. 7B is a view showing a content example of the muscle percentage table 45.

With reference to FIG. 7A, a range of reference values on the body fat percentage and a display width with respect to a reference point (reference value) are stored in correspondence to each other in the body fat percentage table 44. For instance, the display width '(reference value−2.0) % to (reference value+2.0) %' is corresponded to the reference value 'less than 10%' of the body fat percentage. The display width '(reference value−3.0) % to (reference value+3.0) %' is corresponded to the reference value 'greater than or equal to 10% to less than 25%' of the body fat percentage. The display width '(reference value−4.0) % to (reference value+4.0) %' is corresponded to the reference value 'greater than or equal to 25%' of the body fat percentage. In the present embodiment, the display width is defined according to the value of the body fat percentage of the reference. Thus, even if the body fat percentage (reference value) of the reference time point is small, the user can check in detail the degree in change from the reference value.

With reference to FIG. 7B, a range of reference values on the muscle percentage, and a display width with respect to a reference point (reference value) are stored in correspondence to each other in the muscle percentage table 45. For instance, the display width '(reference value−2.0) % to (reference value+2.0) %' is corresponded to the entire range of reference values of the muscle percentage. Therefore, in the present embodiment, a constant display width is defined so that decrease/increase in the muscle percentage can be displayed in detail irrespective of the value of the reference muscle percentage. The display width may be defined depending on the value of the muscle percentage, as in the case of the body fat percentage.

In the present embodiment, the number of blocks included in the first block group is greater than the number of blocks included in the second block group, and thus the variation width per one block (width of the value displayable by one block) becomes smaller on the '−' side than the '+' side. The user thus can recognize in detail the decrease result of the body fat percentage in time of diet.

Even in a case where the number of blocks included in the first block group is greater than the number of blocks included in the second block group, the variation width per one block can be defined so as to be the same for the '−' and the '+' sides in the body fat percentage table 44 and the muscle percentage table 45.

Alternatively, the number of blocks included in the first block group and the number of blocks included in the second block group may be defined as the same number.

<Operation of Body Composition Measuring Instrument According to First Embodiment of the Present Invention>

Figure 8:
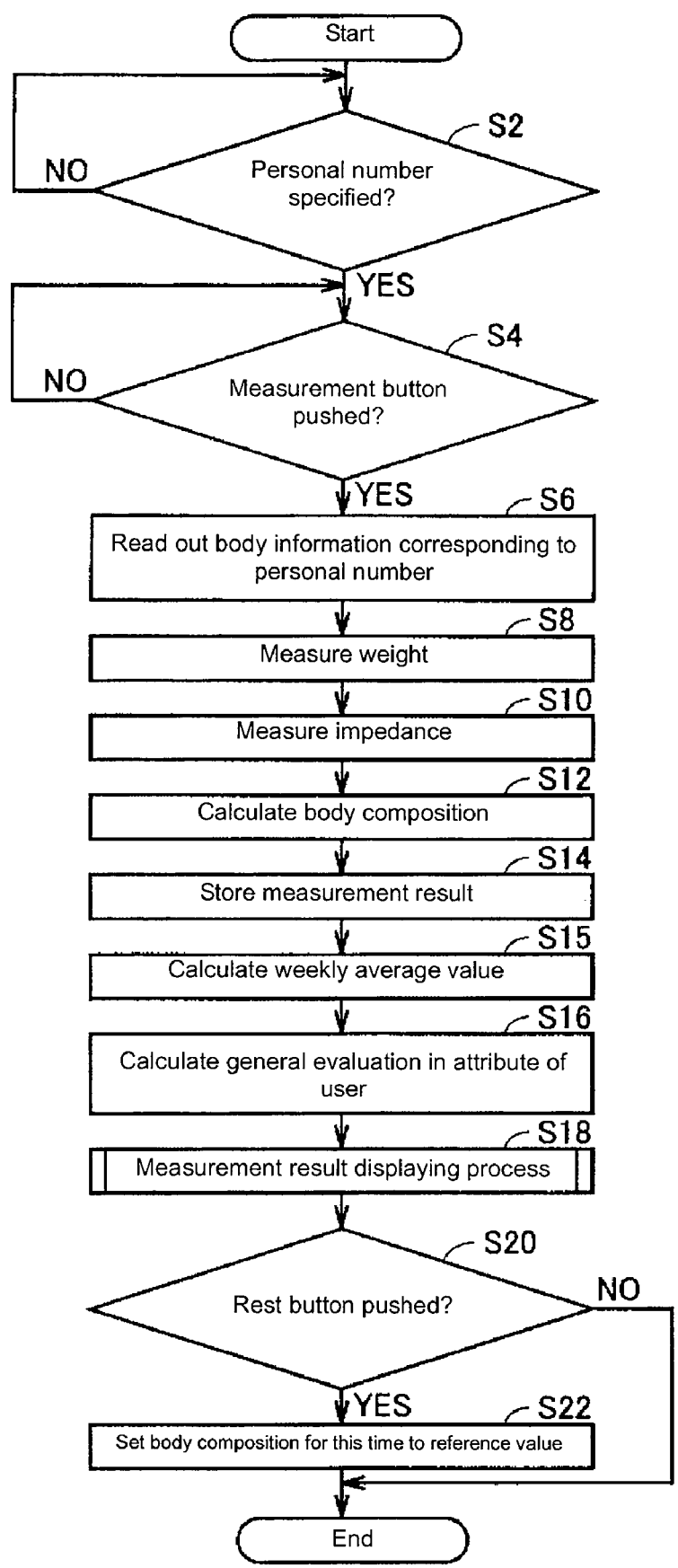
FIG. 8 is a flowchart showing a body composition measuring process executed by the control section of the body composition measuring instrument according to first and second embodiments of the present invention.

FIG. 8 is a flowchart showing a body composition measuring process executed by the control section 12 of the body composition measuring instrument 100 according to the first embodiment of the present invention. The processes shown in the flowchart in FIG. 8 are stored in the memory 14 in advance as a program, wherein the function of the body composition measuring process is realized by having the control section 12 read out and execute the relevant program.

With reference to FIG. 8, the control section 12 first determines whether a personal number is specified by the user (step S2). In other words, whether or not one of the buttons 16H to 16K is pushed by the user is determined. The control section 12 waits until the personal number is specified (NO in step S2). The process proceeds to step S4 when determined that the personal number is specified (YES in step S2).

In step S4, the control section 12 determines whether the measurement button 16C is pushed. The control section 12 waits until the measurement button 16C is pushed (NO in step S4). The process proceeds to step S6 when the measurement button 16C is pushed (YES in step S4).

In step S6, the body composition calculating unit 121 reads out the body information (height, age, sex) corresponding to the personal number specified by the user. For instance, it is assumed that the personal number switch 16H corresponding to personal number 1 is pushed in step S2. In this case, the height data, the age data, and the sex data are read out from the body information storage region 41 in step S6. The read body information is temporarily recorded in the internal memory.

The body composition calculating unit 121 measures the weight based on a signal from the weight measuring section 22 (step S8). The measured weight value is temporarily recorded in the internal memory.

Subsequently, the body composition calculating unit 121 executes the impedance measuring process (step S10). Specifically, the detection section 11 is controlled, and the whole body impedance, the hands impedance, and the feet impedance are measured. The value of the respective measured impedance is temporarily recorded in the internal memory.

The body composition calculating unit 121 calculates the body composition of the user based on each data temporarily recorded in the internal memory, the predetermined calculation formula described above, and the like (step S12). Specifically, the body fat percentage of the whole body, the arm, the torso, and the leg of the user; the muscle percentage of the whole body, the arm, the torso, and the leg; and the age index are calculated. The control section 12 then stores the measurement result, that is, the value of the body composition for this time calculated in step S12 in the measurement result storage region 42 (step S14).

Subsequently, the control section 12 references the measurement result storage region 42 and calculates the weekly average value (step S15). The control section 12 calculates a general evaluation in the attribute of the user (step S16). Specific calculation method in steps S15 and S16 is as described above.

The measurement result displaying process is then executed by the display control unit 122 (step S18). The sub-routine of the measurement result displaying process is shown in FIG. 9.

Figure 9:
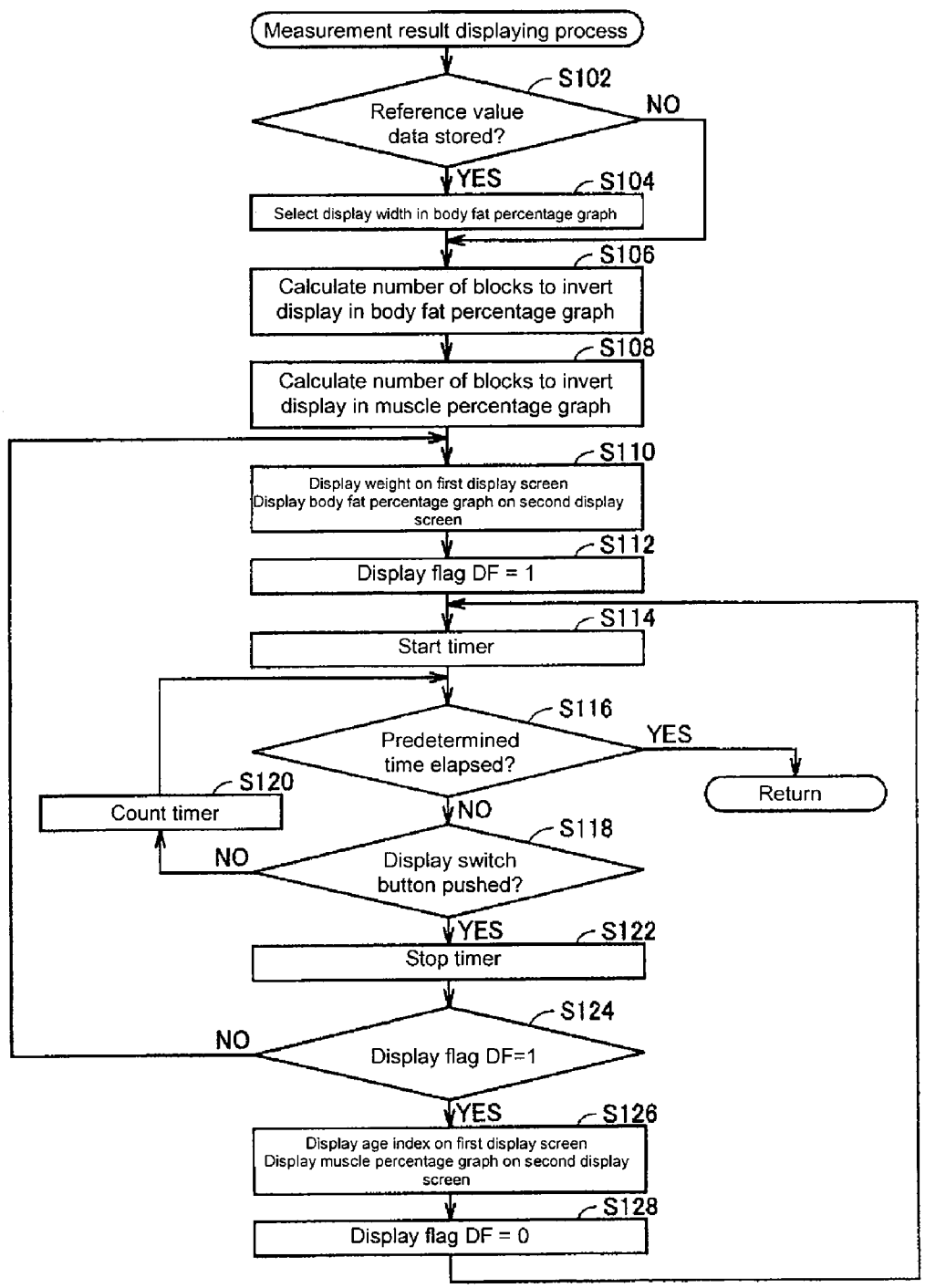
FIG. 9 is a flowchart showing a measurement result displaying process according to the first embodiment and its variant of the present invention.

With reference to FIG. 9, the display control unit 122 first determines whether the reference value data is stored in the reference value storage region 43 corresponding to the specified personal number (step S102). The process proceeds to step S104 if determined that the reference value data is stored (YES in step S102). The process proceeds to step S106 if determined that the reference value data is not stored (NO in step S102).

In step S104, the display control unit 122 selects the display width in the body fat percentage graph. Specifically, the display width in the body fat percentage graph of all of the measuring parts (whole body, arm, torso, and leg) is selected based on the reference value data Fwr of the body fat percentage of the whole body stored in the reference value storage region 43 and the body fat percentage table 44. For instance, if the reference value data Fwr of the body fat percentage of the whole body indicates "22%", the lower limit of the display width in each graph becomes 19% and the upper limit becomes 25%. That is, in this case, the body fat percentage of 19% to 25% is set to be displayable. The process proceeds to step S106 when the process of step S104 is terminated.

In the present embodiment, the display width in the body fat percentage graph of all of the measuring parts is defined based on the reference value of the body fat percentage of the whole body, but it is not limited to such method. The display width of the corresponding graph can be selected for every measuring part. In this case, the range of reference values and the display widths may be stored in correspondence to each other in the display width storage region 145 for every measuring site.

If the display width is defined depending on the value of the reference muscle percentage in the muscle percentage table 45, the display width in the muscle percentage graph of all of the measuring parts is also selected in step S104.

In step S106, the display control unit 122 calculates the number of blocks to invert display in the body fat percentage graph. Specifically, the number of blocks to invert display is calculated based on the measurement value, the reference value, and the display width selected in step S104 for every graph corresponding to each measuring part.

Subsequently, the display control unit 122 calculates the number of blocks to invert display in the muscle percentage graph (step S108). Specifically, the number of blocks to invert display is calculated based on the measurement value, the reference value, and a predetermined display width for every graph corresponding to each measuring site.

If the reference value data is not stored in the reference value storage region 43, the display control unit 122 calculates the number of blocks to invert display based on the measurement value, the standard value in the attribute of the user, and the predetermined display width in steps S106 and S108. In this case, the position of the standard value corresponds to the predetermined fixed position in each graph.

The display control unit 122 then displays the weight on a first display screen 15A of the display section 15, and displays the body fat percentage graph on a second display screen 15B (step S110). An example of a screen display in step S110 is shown in FIG. 10.

Figure 10:
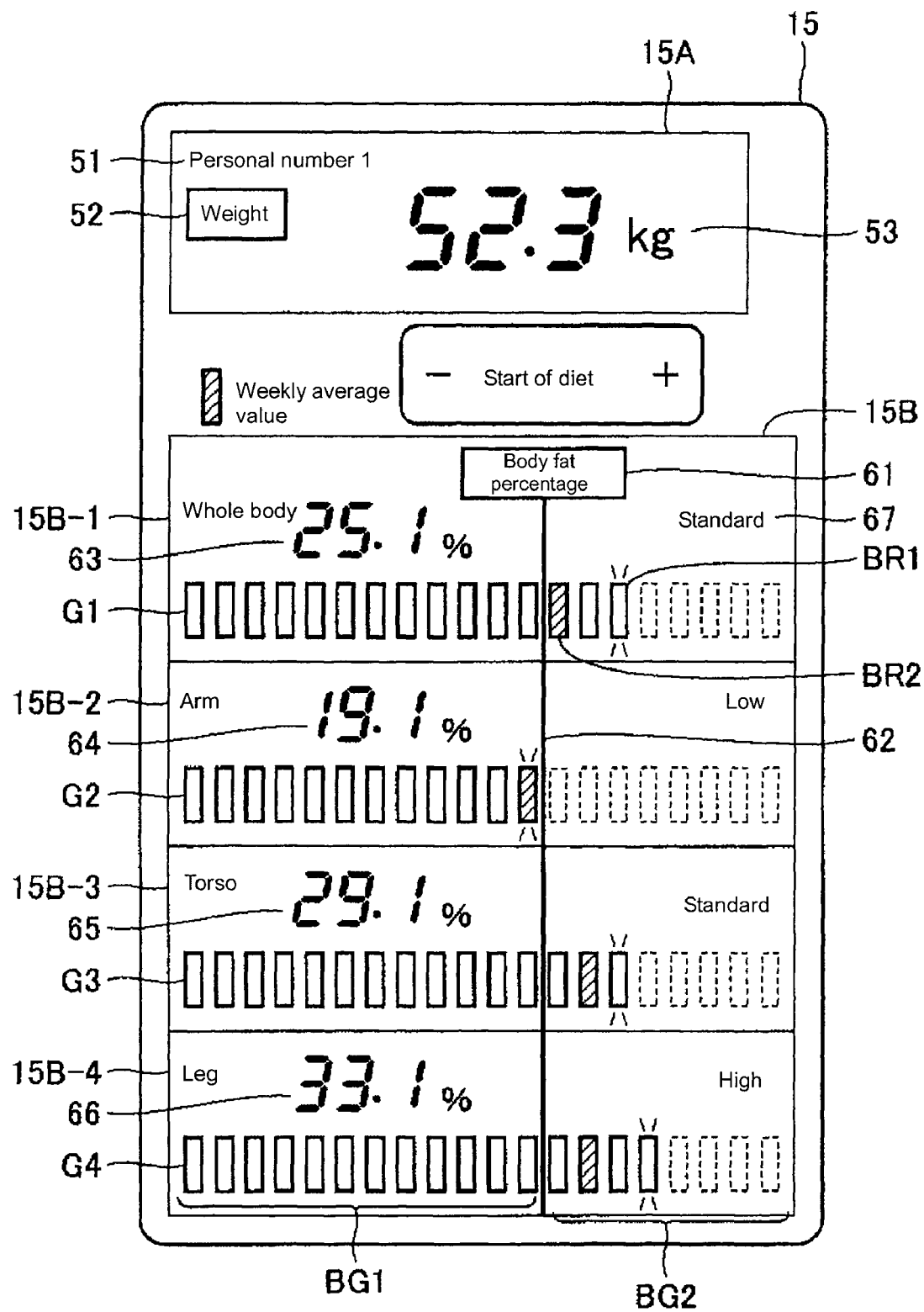
FIG. 10 is a view showing a screen display example in step S110 shown in FIG. 9.

With reference to FIG. 10, information 51 indicating the specified personal number, information 52 indicating that the numerical value being displayed is the weight, and numerical value 53 indicating the measured weight are displayed on the first display screen 15A of the display section 15. The graphs G1, G2, G3, and G4 for the body fat percentage of the whole body, the body fat percentage of the arm, the body fat percentage of the of torso, and the body fat percentage of the leg are respectively displayed in regions 15B-1, 15B-2, 15B-3, and 15B-4 of the second display screen 15B of the display section 15. The regions 15B-1, 15B-2, 15B-3, and 15B-4 respectively display numerical values 63, 64, 65, 66 indicating the body fat percentage for this time. Information 61 indicating that the numerical value and the graph being displayed are related to the body fat percentage is displayed in the second display screen 15B.

The body fat percentage graphs G1, G2, G3, and G4 will be described in detail below.

In the body fat percentage graphs G1, G2, G3, and G4, the position of the reference value is shown by a line 62. The position of the line 62 is fixed irrespective of the reference value and the measurement value. Information (e.g., character "start of diet") capable of identifying that the line 62 corresponds to the position of the reference value is preferably displayed at the same time. Such line 62 is displayed in the present embodiment, but the position of the reference value merely needs to be visually recognized, and it is not limited to such example.

As described above, in each graph G1, G2, G3, and G4, the number of blocks included in the first block group BG1 arranged before ("−" side) the line 62 of the reference value is greater than the number of blocks included in the second block group BG2 arranged after ("+" side) the line 62 of the reference line. Thus, the change in body fat percentage can be displayed in more detail in a case where the body fat percentage for this time becomes smaller than the reference value than a case where it becomes greater than the reference value.

As shown in FIG. 10, the block for the number calculated in step S106 is invert displayed in each graph. Among the invert displayed blocks, the block on the right end, that is, the block BR1 indicating the position of the body fat percentage for this time may be flashing displayed. Furthermore, in each graph, the block BR2 corresponding to the position of the weekly average value calculated in step S15 is displayed with a color different from the display color of other blocks. Furthermore, evaluation information 67 representing the general evaluation in the attribute of the user calculated in step S16 is displayed near each graph.

With reference again to FIG. 9, after the process of step S110, the display control unit 122 sets a display flag DF for identifying the type of body composition being displayed (step S112). Thereafter, the timer is started (step S114), and whether or not a predetermined time has elapsed is determined (step S116). If the predetermined time has not elapsed (NO in step S116), the process proceeds to step S118.

In step S118, the display control unit 122 determines whether the display switch button 16D is pushed. The process proceeds to step S122 if determined that the display switch button 16D is pushed (YES in step S118). If pushing of the display switch button 16D is not detected (NO in step S118), the timer performs counting (step S120), and the process returns to step S116.

In step S122, the display control unit 122 stops the timer. Whether or not the display flag DF is set is determined (step S124). The process proceeds to step S126 if determined that the display flag DF is set (YES in step S124). The process returns to step S110 if determined that the display flag DF is not set (NO in step S124).

In step S126, the display control unit 122 displays the age index on the first display screen 15A of the display section 15, and displays the muscle percentage graph on the second display screen 15B. An example of screen display in step S126 is shown in FIG. 11.

Figure 11:
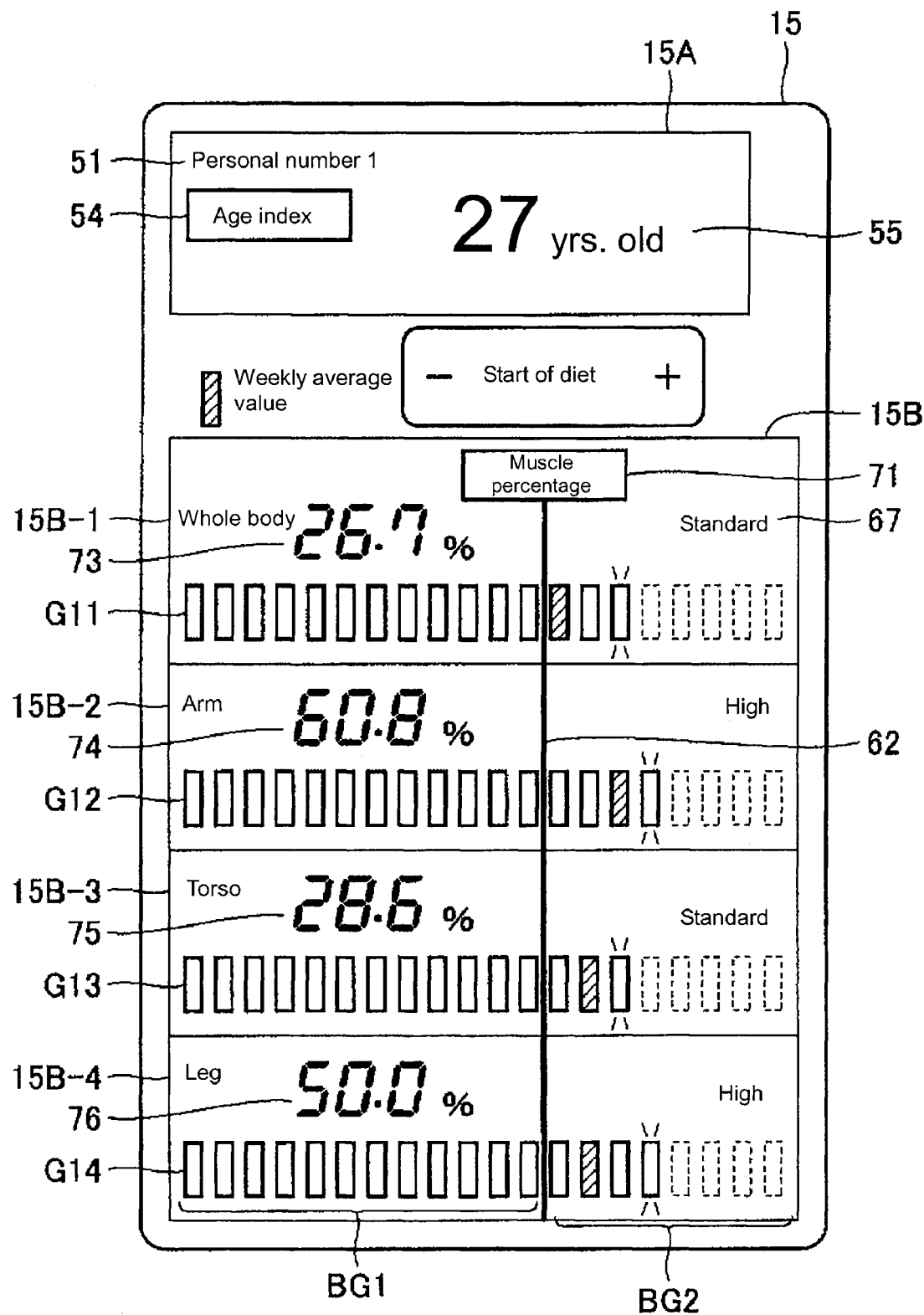
FIG. 11 is a view showing a screen display example in step S126 shown in FIG. 9.

With reference to FIG. 11, information 51 indicating the specified personal number, information 54 indicating that the numerical value being displayed is the age index, and numerical value 55 indicating the calculated age index are displayed on the first display screen 15A of the display section 15. The graphs G11, G12, G13, and G14 for the muscle percentage of the whole body, the muscle percentage of the arm, the muscle percentage of the of torso, and the muscle percentage of the leg are respectively displayed in regions 15B-1, 15B-2, 15B-3, and 15B-4 of the second display screen 15B of the display section 15. These regions 15B-1, 15B-2, 15B-3, and 15B-4 respectively display numerical values 73, 74, 75, 76 indicating the muscle percentage for this time. Information 71 indicating that the numerical value and the graph being displayed are related to the muscle percentage is displayed in the second display screen 15B.

The mode of the muscle percentage graphs G11, G12, G13, and G14 is the same as the body fat percentage graphs G1, G2, G3, and G4. As shown in FIG. 11, the position of the reference value is shown by the line 62 in each graph, and the blocks of the number calculated in step S108 are invert displayed. The line 62 indicating the position of the reference value may differ depending on the type of body composition. For instance, in the case of the muscle percentage, the line 62 may be displayed at a position where the number of blocks contained in the first block group BG1 is the same as the number of blocks contained in the second block group BG2.

Returning to FIG. 9, after the process of step S126, the display control unit 122 clears the display flag DF (step S128) and the process returns to step S114. Thus, every time the user pushes the display switch button 16D, the information of the body composition of the type desired by the user is displayed. Here, when the display switch button 16D is pushed, the displays of both the first display screen 15A and the second display screen 15B are switched, but the displays do not need to be simultaneously switched.

If the pushing of the display switch button 16D is not detected for a predetermined time, that is, if the predetermined time has elapsed in step S116 (YES in step S116), the process returns to the main routine.

With again reference to FIG. 8, the control section 12 determines whether the reset button 16E is pushed (step S20) after the measurement result displaying process (step S18). If the pushing of the reset button 16E is detected (YES in step S20), the process proceeds to step S22. If the pushing of the reset button 16E is not detected for a predetermined time in step S20 (NO in step S20), the series of measuring processes are terminated.

In step S22, the reference value storage processing unit 123 sets the body composition for this time as the reference value. That is, if information of the reference value is not stored in the reference value storage region 43 (if setting of reference value is not performed even once in the past), the value of the body composition calculated in step S12 is stored in the reference value storage region 43. If the information of the reference value is stored in the reference value storage region 43 (if setting of the reference value is performed in the past), the reference value is updated to the value of the body composition calculated in step S12. Thus, when the reset button 16E is pushed, the subsequent measurement results are displayed with the body composition for this time as the reference (this time is the reference time point). The series of measuring process is terminated when the process of step S22 is terminated.

As described above, according to the present embodiment, the range of values of the body composition that can be displayed can be freely varied since the reference value can be reset. The change from the reference value can be displayed according to the plan of the user himself/herself such as long-term diet and short-term diet. Furthermore, since the position of the reference value is fixed, the detailed change can be displayed for every user even if the display region in the display section 15 is small.

If the reset button 16E is pushed in the middle of the measurement result displaying process shown in FIG. 9, the process proceeds to step S22 of the main routine.

As described above, the setting/updating of the reference value is performed when the reset button 16E is pushed by the user in the body composition measuring process in the present embodiment. However, the setting/updating of the reference value is not limited to such case, and the measurement data being a reference can be selected by the user from the past measurement data. For instance, the control section 12 reads out the past measurement data stored in the measurement result storage region 42 when detecting the pushing of the memory button 16B, and displays the same on the display section 15. In this case, when the reset button 16E is pushed by the user, the reference value storage processing unit 123 may set/updated the value of the body composition corresponding to the measurement data being selected by the cursor as the reference value.

Furthermore, in the present embodiment, the display width of the graph is selected based on the reference value for every measurement result displaying process, but the method is not limited thereto. The information of the display width of each graph may be stored in a corresponding manner in the reference value storage region 43 when performing the process of storing the reference value (step S22). In this case, in step S104, the display control unit 122 determines the display width in the body fat percentage graph based on the information of the display width stored in the reference value storage region 43.

In the first embodiment, the setting/updating of the reference value is not performed until being specified by the user. The time point desired by the user thus can be set as the reference time point. However, the setting/updating of the reference value is not limited to such timing. For instance, the first measurement value of each user may be automatically set as the reference value.

Alternatively, the setting/updating of the reference value may be performed at a timing shown in the variant below. In the description of the variant below, same reference numerals as the body composition measuring instrument 100 in the first embodiment are used.

(First Variant)

The first variant of the first embodiment will be described with reference to FIG. 12.

Figure 12:
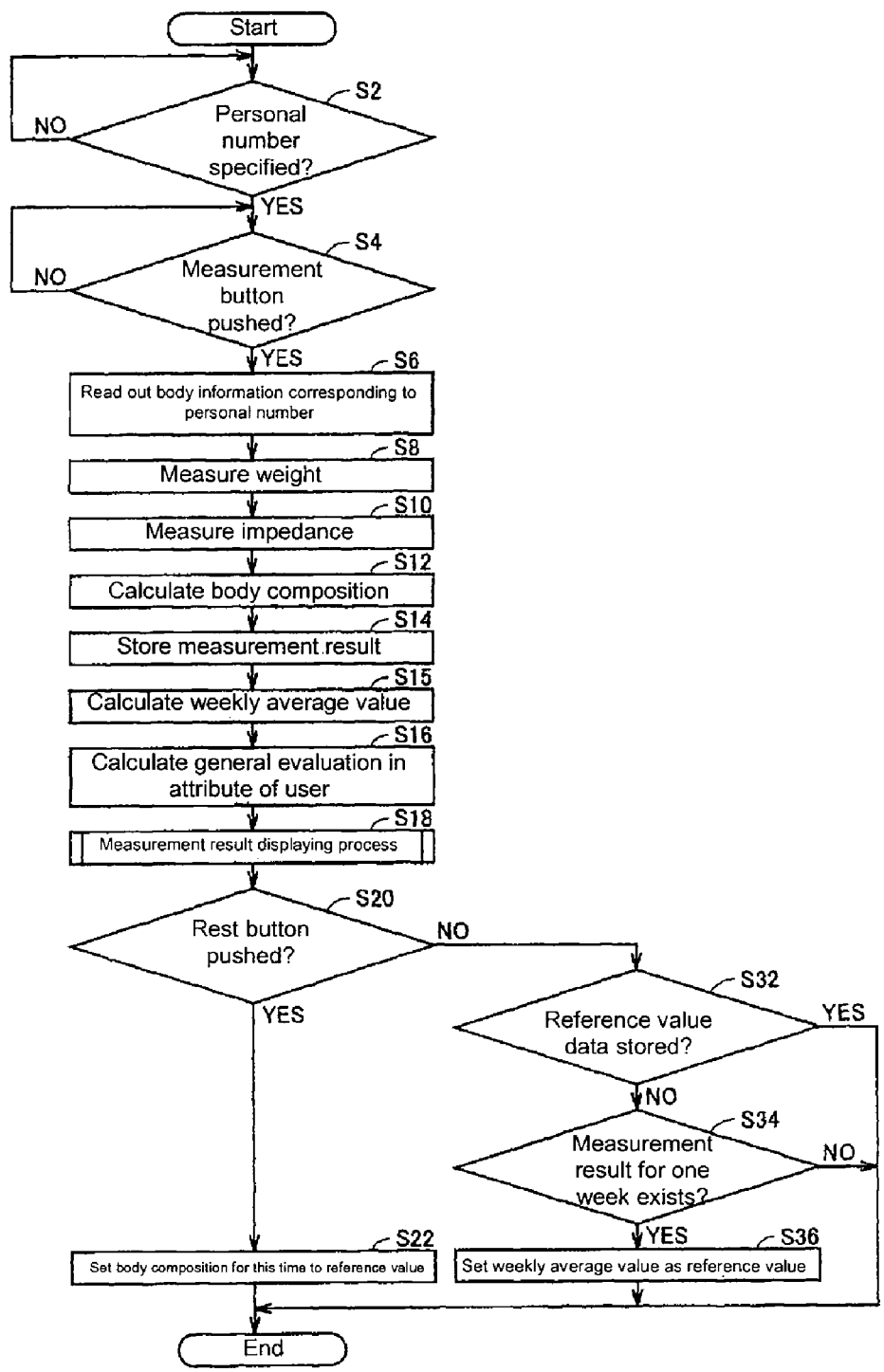
FIG. 12 is a flowchart showing a body composition measuring process executed by the control section of the body composition measuring instrument according to a first variant of the first embodiment of the present invention.

FIG. 12 is a flowchart showing a body composition measuring process executed by the control section 12 of the body composition measuring instrument 100 according to the first variant of the first embodiment of the present invention. The processes similar to the body composition measuring process shown in FIG. 8 of the first embodiment are denoted with the same step numbers, and the description thereof will not be repeated.

In the first variant, the process proceeds to step S32 if the pushing of the reset button 16E is not detected for a predetermined time in step S20 (NO in step S20). In step S32, the reference value storage processing unit 123 determines whether or not the reference value data is stored in the reference value storage region 43 corresponding to the specified personal number. If determined that the reference value data is stored (YES in step S32), the measuring process is terminated. If determined that the reference value data is not stored (NO in step S32), the process proceeds to step S34.

In step S34, the reference value storage processing unit 123 references the measurement result storage region 42 and determines whether the measurement result for a predetermined period (e.g., one week) exists. If determined that the measurement result for one week does not exist (NO in step S34), the measuring process is terminated. If determined that the measurement result for one week exists (YES in step S34), the process proceeds to step S36.

In step S36, the reference value storage processing unit 123 sets the weekly average value as the reference value. More specifically, the reference value storage processing unit 123 stores the weekly average value calculated in step S15 in the reference value storage region 43 as the reference value. The measuring process is terminated when the process of step S36 is terminated.

According to the first variant of the first embodiment, if the specification of the reference value is not made by the user for a predetermined period (e.g., one week), the average value of the relevant period is set as the reference value. Thus, the reference value can be automatically set even if the user does not understand the operating method of the reset button 16E.

Whether to set the weekly average value as the reference value can be inquired to the user before setting the weekly average value as the reference value in step S36.

(Second Variant)

The second variant of the first embodiment will be described with reference to FIG. 13.

Figure 13:
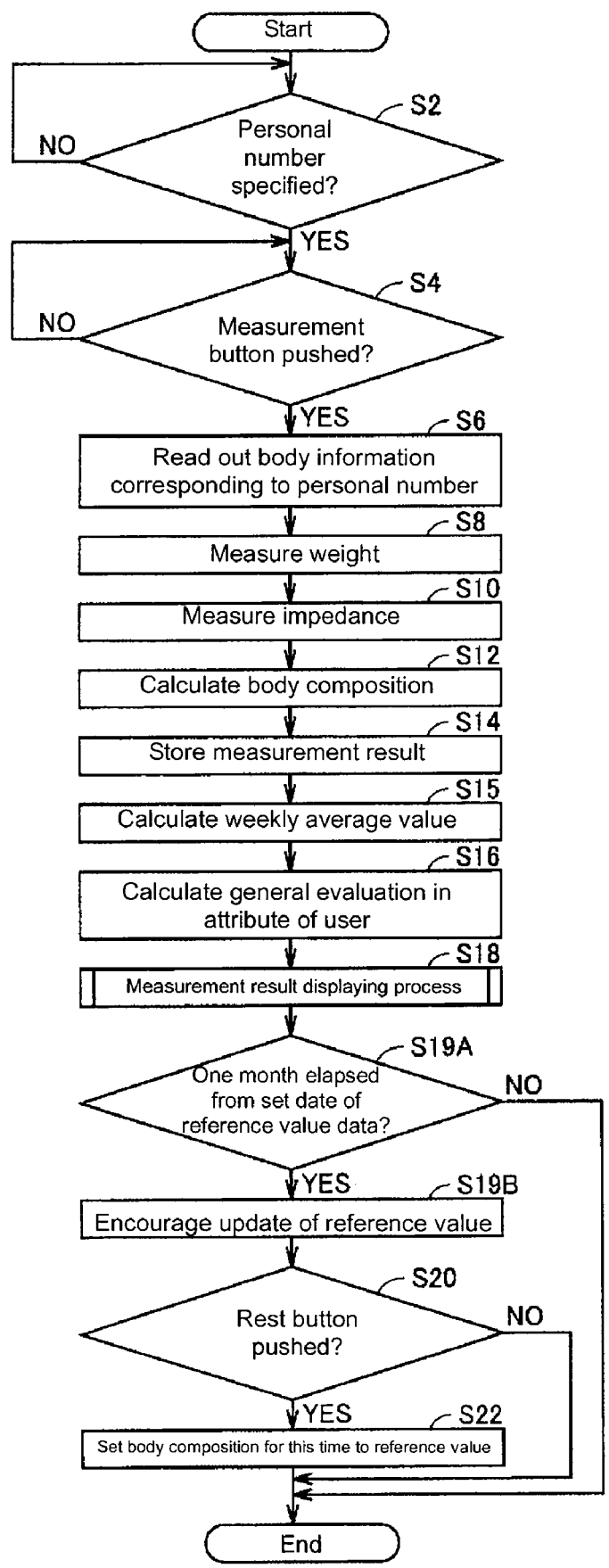
FIG. 13 is a flowchart showing a body composition measuring process executed by the control section of the body composition measuring instrument according to a second variant of the first embodiment of the present invention.

FIG. 13 is a flowchart showing a body composition measuring process executed by the control section 12 of the body composition measuring instrument 100 according to the second variant of the first embodiment of the present invention. The processes similar to the body composition measuring process shown in FIG. 8 of the first embodiment are denoted with the same step numbers, and the description thereof will not be repeated.

In the second variant, the processes of steps S19A, S19B are added between the step S18 (measurement result displaying process) and the step S20 (determination process on whether or not the reset button is pushed).

In step S19A, the control section 12 references the date and time data DTr of the reference value storage region 43, and determines whether a predetermined period (e.g., one month) has elapsed from the set date of the reference value data. If determined that one month has elapsed from the set date (YES in step S19A), the process proceeds to step S19B. If determined that one month has not elapsed from the set date (NO in step S19A), the measuring process is terminated.

In step S19B, the control section 12 encourages the update of the reference value. Specifically, for example, a message such as "Update of reference value is recommended" is displayed on the display section 15 to notify the user to update the reference value.

The process proceeds to step S20 described above once the process of step S19B is terminated.

For instance, the health is preferably managed in units of one to three months when reducing weight to improve lifestyle-related diseases. According to the second variant of the first embodiment, notification to update the reference value is made to the user when the predetermined period (e.g., one month) has elapsed from the set date of the reference value data. Thus, the user can easily carry out health management in units of a predetermined period.

(Third Variant)

The third variant of the first embodiment will be described with reference to FIG. 14.

Figure 14:
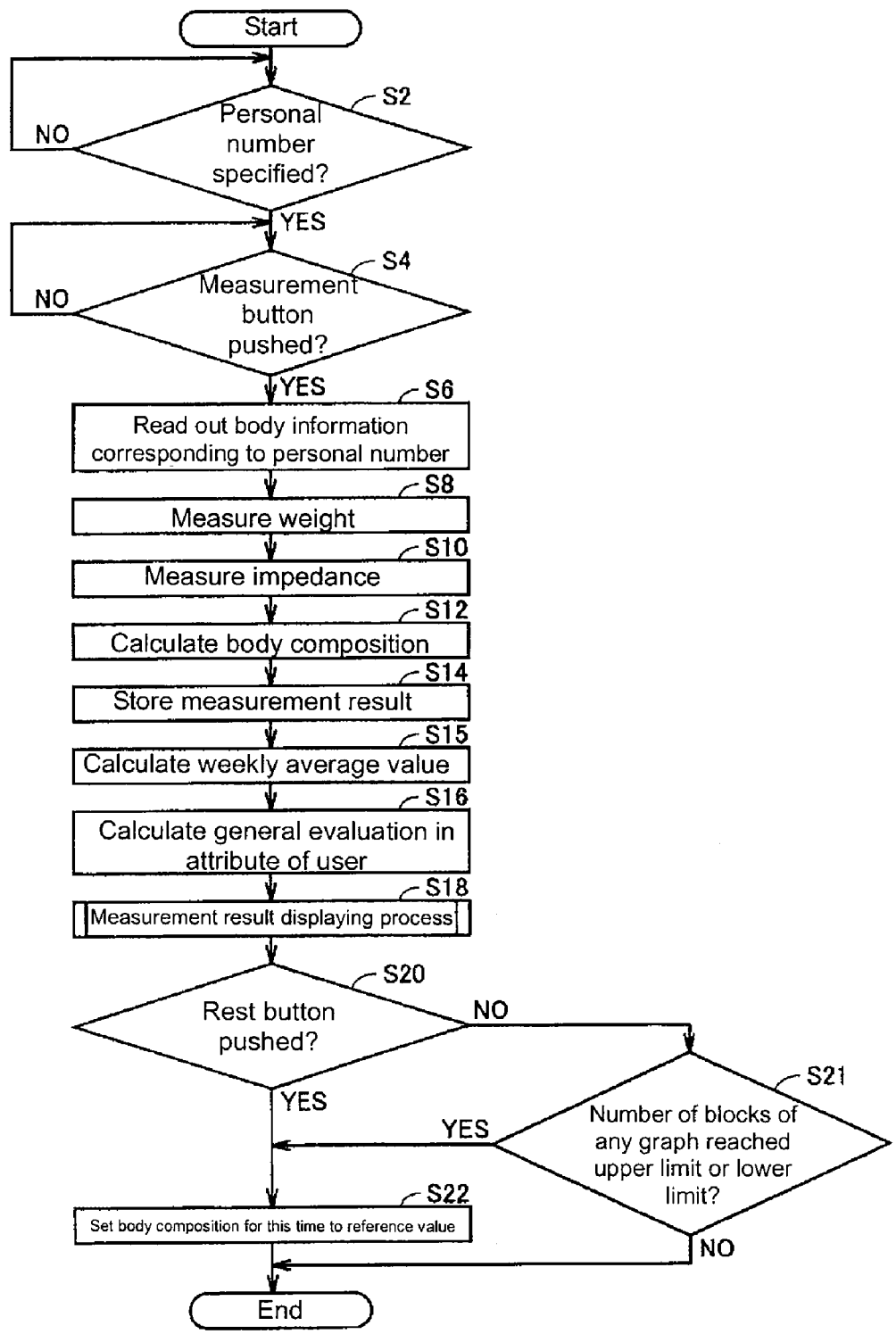
FIG. 14 is a flowchart showing a body composition measuring process executed by the control section of the body composition measuring instrument according to a third variant of the first embodiment of the present invention.

FIG. 14 is a flowchart showing a body composition measuring process executed by the control section 12 of the body composition measuring instrument 100 according to the third variant of the first embodiment of the present invention. The processes similar to the body composition measuring process shown in FIG. 8 of the first embodiment are denoted with the same step numbers, and the description thereof will not be repeated.

In the third variant, the process proceeds to step S21 when pushing of the reset button 16E is not detected for a predetermined time in step S20 (NO in step S20). In step S21, the control section 12 determines whether the value of the body fat percentage or the value of the muscle percentage for this time has reached an upper limit or a lower limit of a displayable range in each graph. That is, whether or not the number of blocks in at least either one of the body fat percentage graph and the muscle percentage graph has reached the upper limit or the lower limit is determined. Specifically, since each graph includes twenty blocks in the third variant of the first embodiment of the present invention, whether or not the number of blocks calculated in step S106 or the number of blocks calculated in step S108 is one or twenty is determined.

If determined that the value of the body fat percentage or the value of the muscle percentage for this time has reached the upper limit or the lower limit of the displayable range in each graph (YES in step S21), the process proceeds to step S22 described above. If determined that both the value of the body fat percentage and the value of the muscle percentage for this time have not reached the upper limit or the lower limit of the displayable range in each graph (NO in step S21), the measuring process is terminated.

The reference value is automatically updated when at least either one of the value of the body fat percentage and the value of the muscle percentage for this time has reached the upper limit or the lower limit of the displayable range in each graph, and in this case, the user may be encouraged to update the reference value. In the third variant, the reference value is updated when at least either one of the value of the body fat percentage and the value of the muscle percentage has reached the upper limit or the lower limit of the displayable range at least once in each graph, but the reference value may be updated only when reaching the upper limit or the lower limit of the displayable range for two or more times.

(Fourth Variant)

The fourth variant of the first embodiment will be described with reference to FIG. 15.

Figure 15:
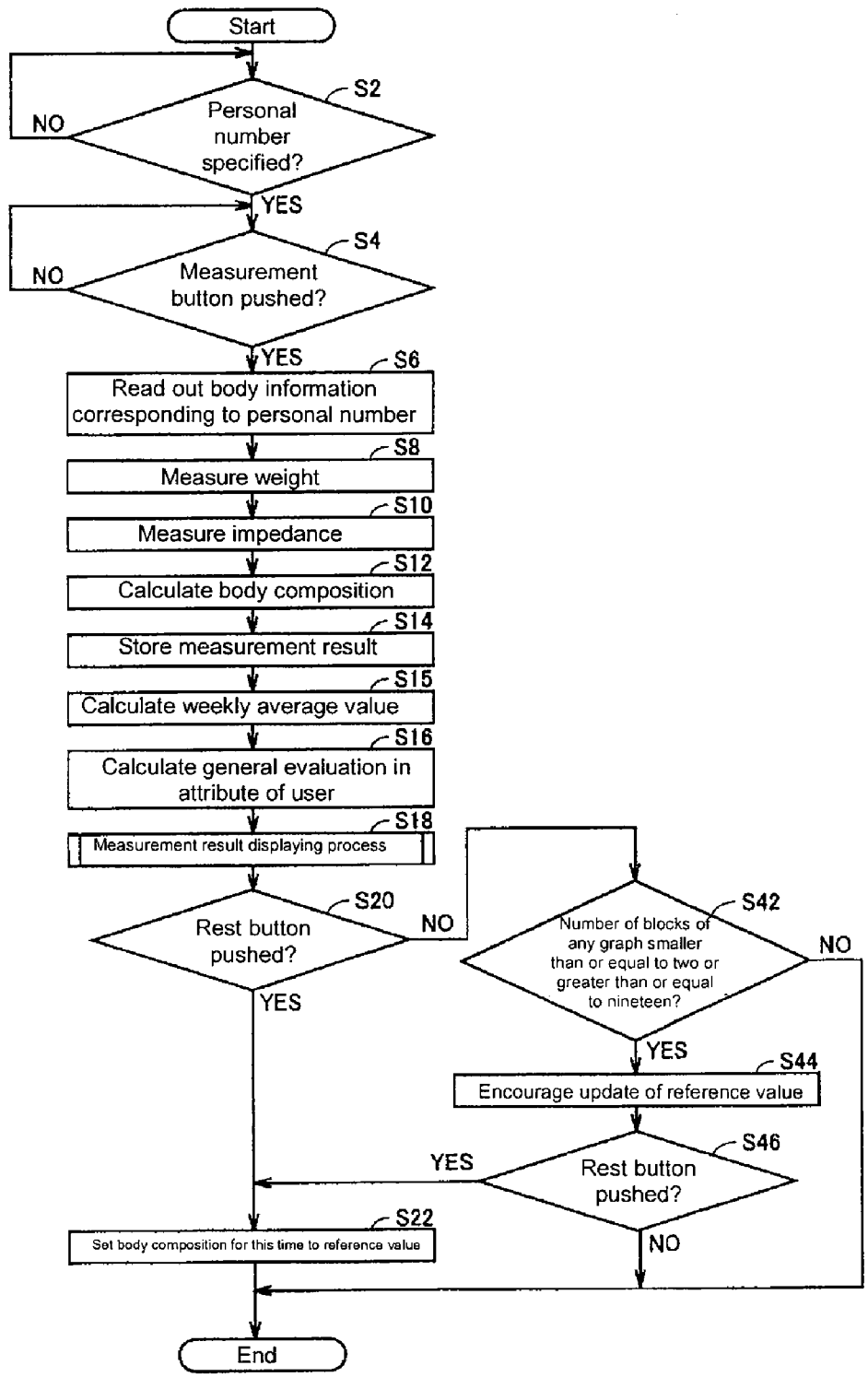
FIG. 15 is a flowchart showing a body composition measuring process executed by the control section of the body composition measuring instrument according to a fourth variant of the first embodiment of the present invention.

FIG. 15 is a flowchart showing a body composition measuring process executed by the control section 12 of the body composition measuring instrument 100 according to the fourth variant of the first embodiment of the present invention. The processes similar to the body composition measuring process shown in FIG. 8 of the first embodiment are denoted with the same step numbers, and the description thereof will not be repeated.

In the fourth variant, the process proceeds to step S42 when the pushing of the reset button 16E is not detected for a predetermined time in step S20 (NO in step S20). In step S42, the control section 12 determines whether the value of the body fat percentage or the value of the muscle percentage for this time has approached the upper limit or the lower limit of the displayable range in each graph. That is, whether or not the number of blocks of at least either one of the body fat percentage graph and the muscle percentage graph has reached 'upper limit−predetermined number' or 'lower limit+ predetermined number' is determined. Specifically, since each graph includes twenty blocks in the fourth variant of the first embodiment of the present invention, whether or not the number of blocks calculated in step S106 or the number of blocks calculated in step S108 is smaller than or equal to two or greater than or equal to nineteen is determined.

If determined that both the value of the body fat percentage and the value of the muscle percentage for this time have not approached the upper limit or the lower limit of the displayable range in each graph (NO in step S42), the measuring process is terminated. If determined that the value of the body fat percentage or the value of the muscle percentage for this time has reached the upper limit or the lower limit of the displayable range in each graph (YES in step S42), the process proceeds to step S44.

In step S44, the control section 12 encourages the update of the reference value. Specifically, for example, a message such as "Update of reference value is recommended" is displayed on the display section 15 to notify the user to update the reference value.

The control section 121 then again determines whether the reset button 16E is pushed (step S46). If determined that the reset button 16E is pushed (YES in step S46), the process proceeds to step S22. If the pushing of the reset button 16E is not detected (NO in step S46), the measuring process is terminated.

The processes of steps S42 to S46 are performed when the reset button 16E is not pushed by the user after the measurement result displaying process (S18), but the procedure is not limited thereto. The processes of steps S42 and S44 may be inserted between the processes of the measurement result displaying process (S18) and step S20. In this case, the process of step S46 becomes unnecessary.

Second Embodiment

In the first embodiment and the first to fourth variants, what extent the measurement value has changed from the reference value can be notified to the user by displaying the position of the measurement value and the position of the reference value on a predetermined graph. In the second embodiment, information indicating whether or not the measurement value has approached the target value set by the user is displayed.

In the second embodiment, the measurement result displaying process differs from the first embodiment. The configuration and the basic operation of the body composition measuring instrument of the second embodiment are similar to the body composition measuring instrument of the first embodiment. Therefore, the difference with the first embodiment will be described citing the reference numerals used for the first embodiment.

A target value storage region (not shown) for storing the input target value is further included for every user in the regions 141 to 144 of the memory 14 of the second embodiment.

Figure 16:
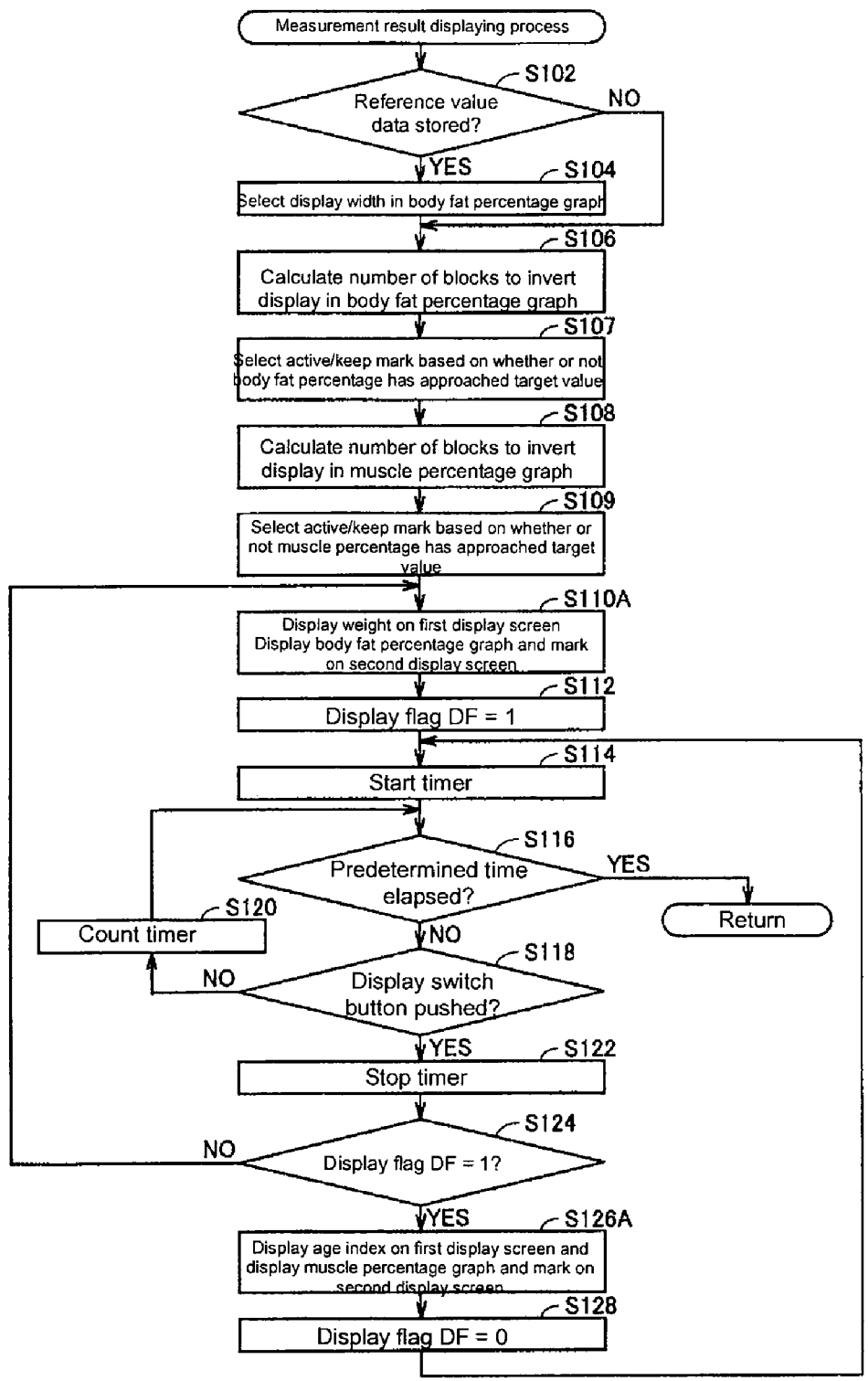
FIG. 16 is a flowchart showing a measurement result displaying process according to a second embodiment of the present invention.

FIG. 16 is a flowchart showing a measurement result displaying process according to the second embodiment of the present invention. In the first embodiment, the same step numbers are denoted for the processes similar to the measurement result displaying process shown in FIG. 9 in the first embodiment, and the description thereof will not be repeated.

With reference to FIG. 16, step S107 is inserted between step S106 and step S108. Furthermore, step S109 is inserted between step S108 and S110 (herein, S110A). The process of step S110A is performed in place of step S110, and the process of step S126A is performed in place of step S126.

In step S107, the display control unit 122 selects either one of an active mark or a keep mark based on whether or not the body fat percentage for this time has approached the target value. The active mark is a predetermined symbol mark indicating that the value is approaching the target value, and the keep mark is a predetermined symbol mark indicating that the value is not approaching the target value. In step S107, specifically, the active mark is selected when the value of the body fat percentage of the whole body for this time is approaching the target value than the measurement value of the body fat percentage of the whole body for the previous time. On the contrary, the keep mark is selected when the value of the body fat percentage of the whole body for this time is not approaching the target value than the measurement value of the body fat percentage of the whole body for the previous time.

In step S109, the display control unit 122 selects either one of an active mark or a keep mark based on whether or not the muscle percentage for this time has approached the target value. In step S109, specifically, the active mark is selected when the value of the muscle percentage of the whole body for this time is approaching the target value than the measurement value of the muscle percentage of the whole body for the previous time. On the contrary, the keep mark is selected when the value of the muscle percentage of the whole body for this time is not approaching the target value than the measurement value of the muscle percentage of the whole body for the previous time.

As a result, in step S110A, the display control unit 122 displays the weight for this time on the first display screen 15A as in the first embodiment, and displays the mark selected in step S107 along with the body fat percentage graph on the second display screen 15B. In step S126A, the display control unit 122 displays the age index for this time on the first display screen 15A as in the first embodiment, and displays the mark selected in step S109 along with the muscle percentage graph on the second display screen 15B.

Figure 17:
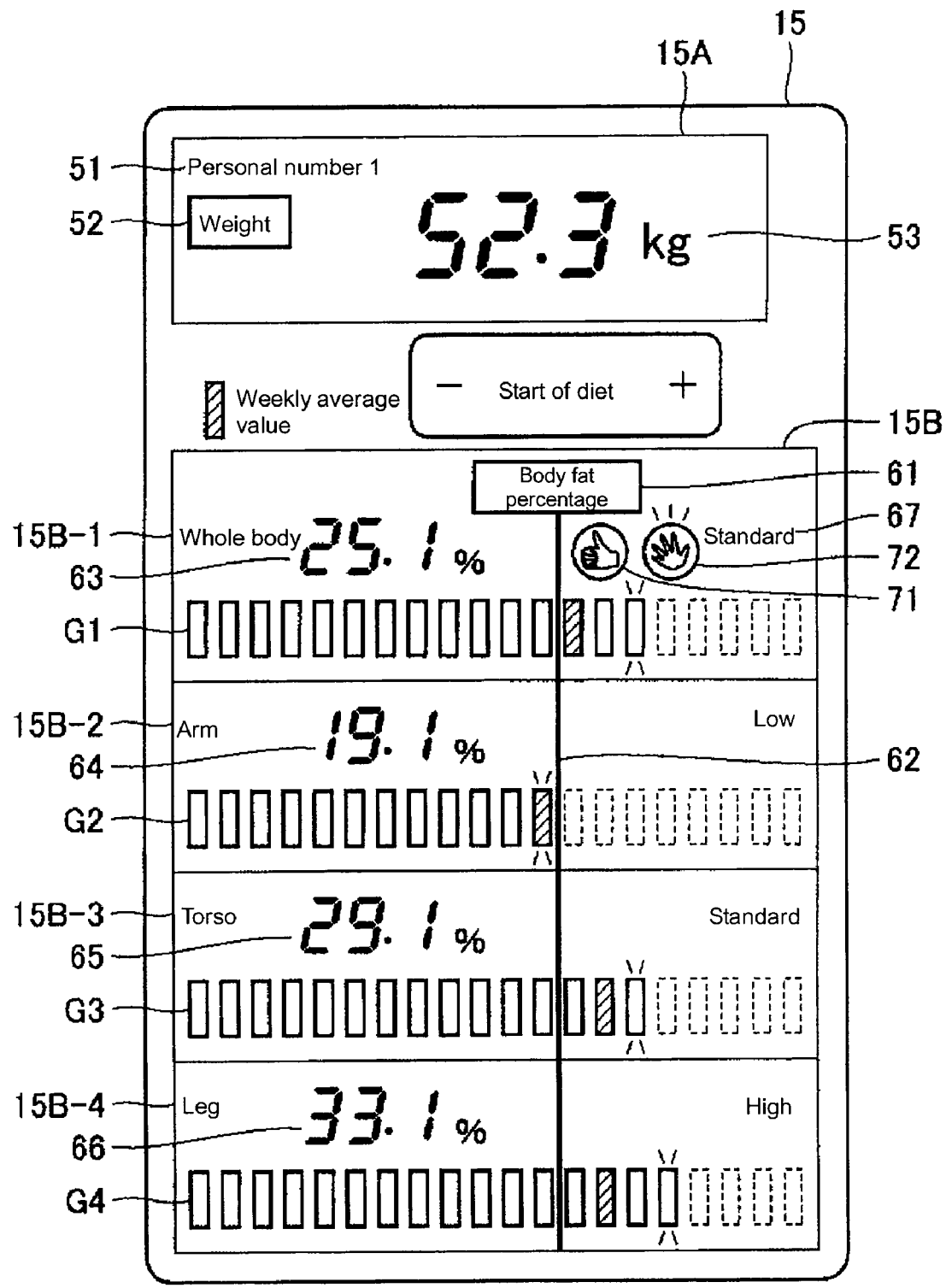
FIG. 17 is a view showing an example of screen display in step S110A shown in FIG. 16.

An example of screen display in step S110A is shown in FIG. 17.

With reference to FIG. 17, in a region 15B-1 of the second display screen 15B of the display section 15, the active mark 72 is flashing displayed, and the keep mark 71 is non-flashing displayed (gray out). The fact that the body fat percentage of the whole body for this time is closer to the target value than the previous time is notified to the user.

Also in step S126A, the active/keep mark is displayed similar to FIG. 17.

Therefore, in the present embodiment, in addition to showing the extent of change of the value of the body composition for this time from the reference value, whether or not the value of the body composition for this time is approaching the target value can be notified. Therefore, the user can understand in detail how the value of his/her body composition is changing.

The mode of the active/keep mark is not limited to the mode shown in FIG. 17.

In the second embodiment, the comparing target of whether or not the value of the body composition for this time is approaching the target value has been described with the measurement value for the previous time by way of example, but is not limited to the previous time. The comparing target merely needs to be a value related to the measurement before this time, and may be a weekly average value and the like.

In the second embodiment, the active/keep mark is selected based on whether or not the value of the body composition for this time has approached the target value than before. However, the active/keep mark may be selected based on the conditions in the variant below.

(Variant)

In a variant of the second embodiment, the display control unit 122 selects the active/keep mark based on whether or not the body composition for this time has changed to a desirable tendency than before.

Figure 18:
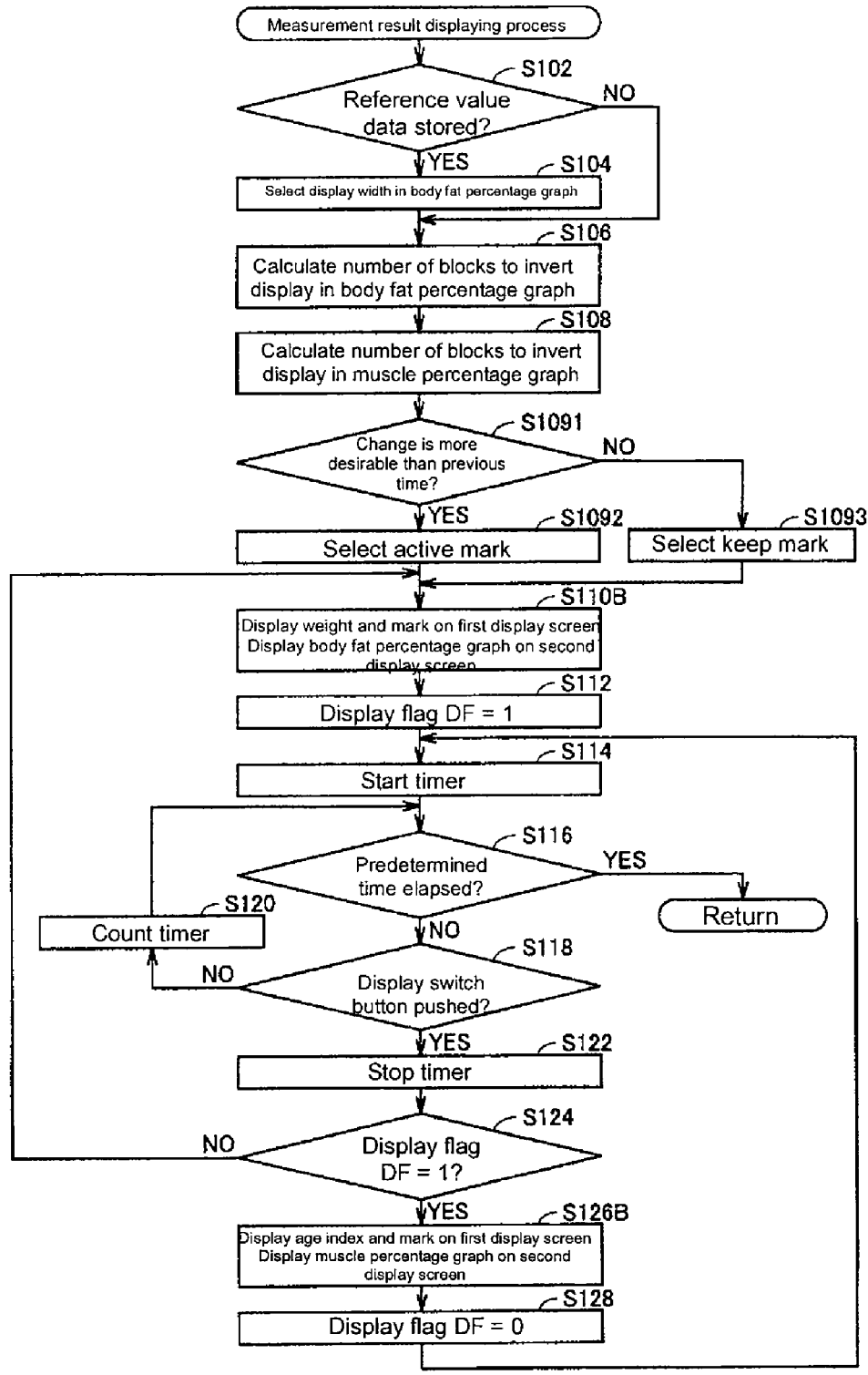
FIG. 18 is a flowchart showing a measurement result displaying process according to a variant of the second embodiment of the present invention.

FIG. 18 is a flowchart showing a measurement result displaying process according to the variant of the second embodiment of the present invention. The same step numbers are denoted for the processes similar to the measurement result displaying process shown in FIG. 9 in the first embodiment, and the description thereof will not be repeated.

With reference to FIG. 18, steps S1091 to S1093 are inserted between step S108 and step S110 (herein, S110B) in the variant of the second embodiment. The process of step S110B is performed in place of step S110, and the process of step S126B is performed in place of step S126.

In step S1091, the display control unit 122 determines whether or not the change is more desirable than the previous time. For instance, if the body fat tends to decrease and the muscle tends to increase than the previous time, the change is determined as desirable. More specifically, determination is made as a desirable change when the following conditional equation is met.

$p2-p1 \geq 2[\%]$ $p1 = \{(\text{muscle percentage for previous time})/(\text{muscle percentage for previous time+body fat percentage for this time})\} \times 100$ $p2 = \{(\text{muscle percentage for this time})/(\text{muscle percentage for this time+body fat percentage for this time})\} \times 100$ For instance, if the muscle percentage for the previous time is 35%, the body fat percentage for the previous time is 20%, the muscle percentage for this time is 30%, and the body fat percentage for this time is 25%, $p2-p1=-9.1$, and thus the display control unit 122 determines that the change is not a desirable change.

If the muscle percentage for the previous time is 30%, the body fat percentage for the previous time is 27%, the muscle percentage for this time is 33%, and the body fat percentage for this time is 23%, $p2-p1=6.3$, and thus the display control unit 122 determines that the change is a desirable change.

If determined as a desirable change than the previous time in step S1091 (YES in step S1091), the display control unit 122 selects the active mark (S1092). If determined as not a desirable change than the previous time (NO in step S1091), the display control unit 122 selects the keep mark (S1093).

As a result, in step S110B, the display control unit 122 displays the weight for this time and the selected mark on the first display screen 15A, and displays the body fat percentage graph as in the first embodiment on the second display screen 15B. In step S126B, the display control unit 122 displays the age index for this time and the selected mark on the first display screen 15A, and displays the muscle percentage graph as in the first embodiment on the second display screen 15B.

Thus, also in the variant of the second embodiment, in addition to showing the extent of change of the value of the body composition for this time from the reference value, whether or not the value of the body composition for this time is changing in a tendency more desirable than before can be notified. Therefore, the user can understand in detail how the value of his/her body composition is changing.

Also in the variant of the second embodiment, the comparing target on whether or not the change is desirable is described with the measurement value for the previous time by way of example, but is not limited to the previous time. The comparing target merely needs to be a value related to the measurement before this time, and may be a weekly average value and the like.

Figure 19:
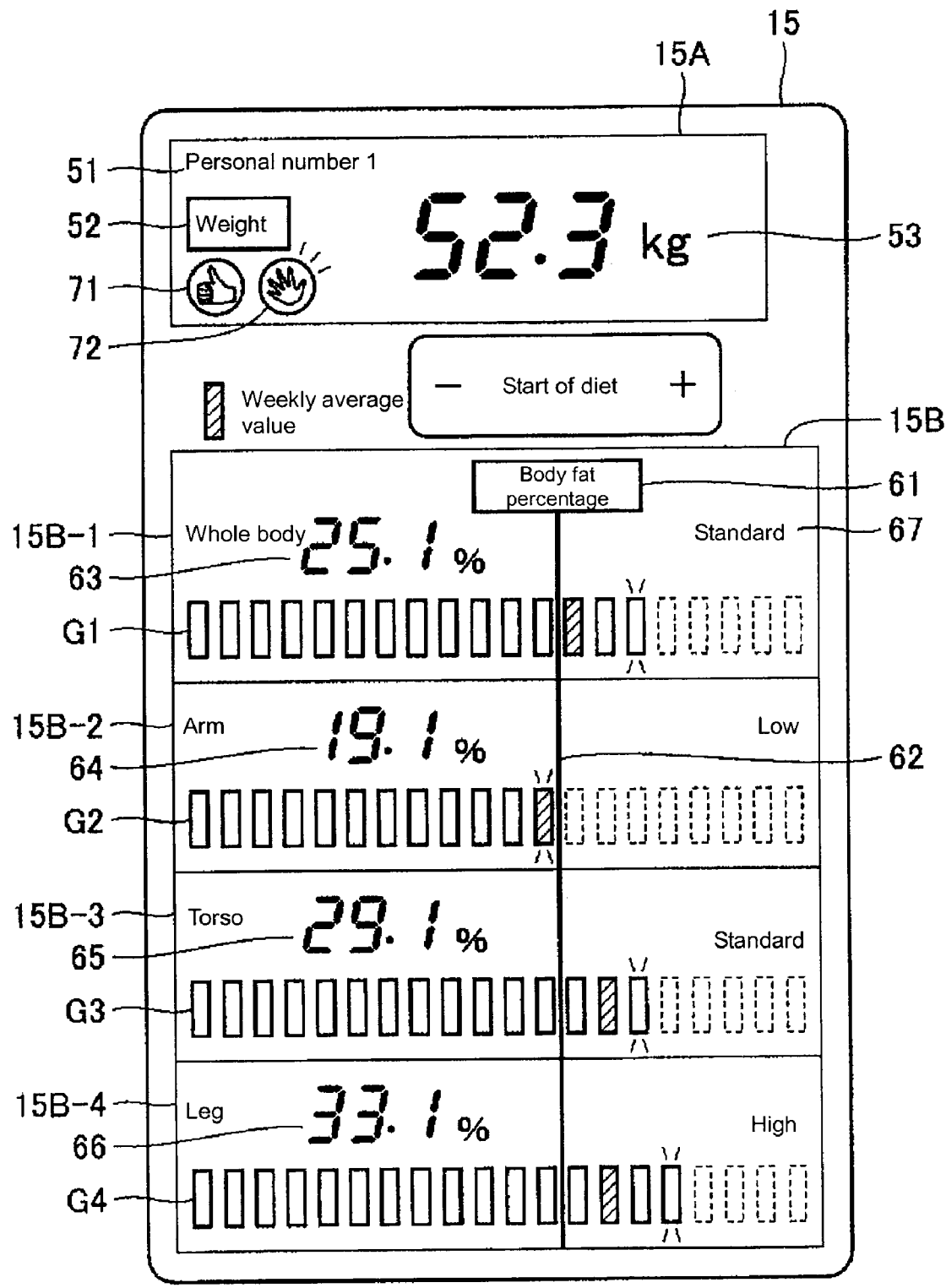
FIG. 19 is a view showing an example of screen display in step S110B shown in FIG. 18.

An example of screen display in step S110B is shown in FIG. 19.

With reference to FIG. 19, the active mark 72 is flashing displayed on the first display screen 15A of the display section 15, and the keep mark 71 is non-flashing displayed (gray out). The fact that the measurement value for this time is changing in a tendency more desirable than the previous time is thus notified to the user.

In step S126B as well, the active/keep mark may be displayed on the first display screen 15A, similar to FIG. 19.

Figure 20:
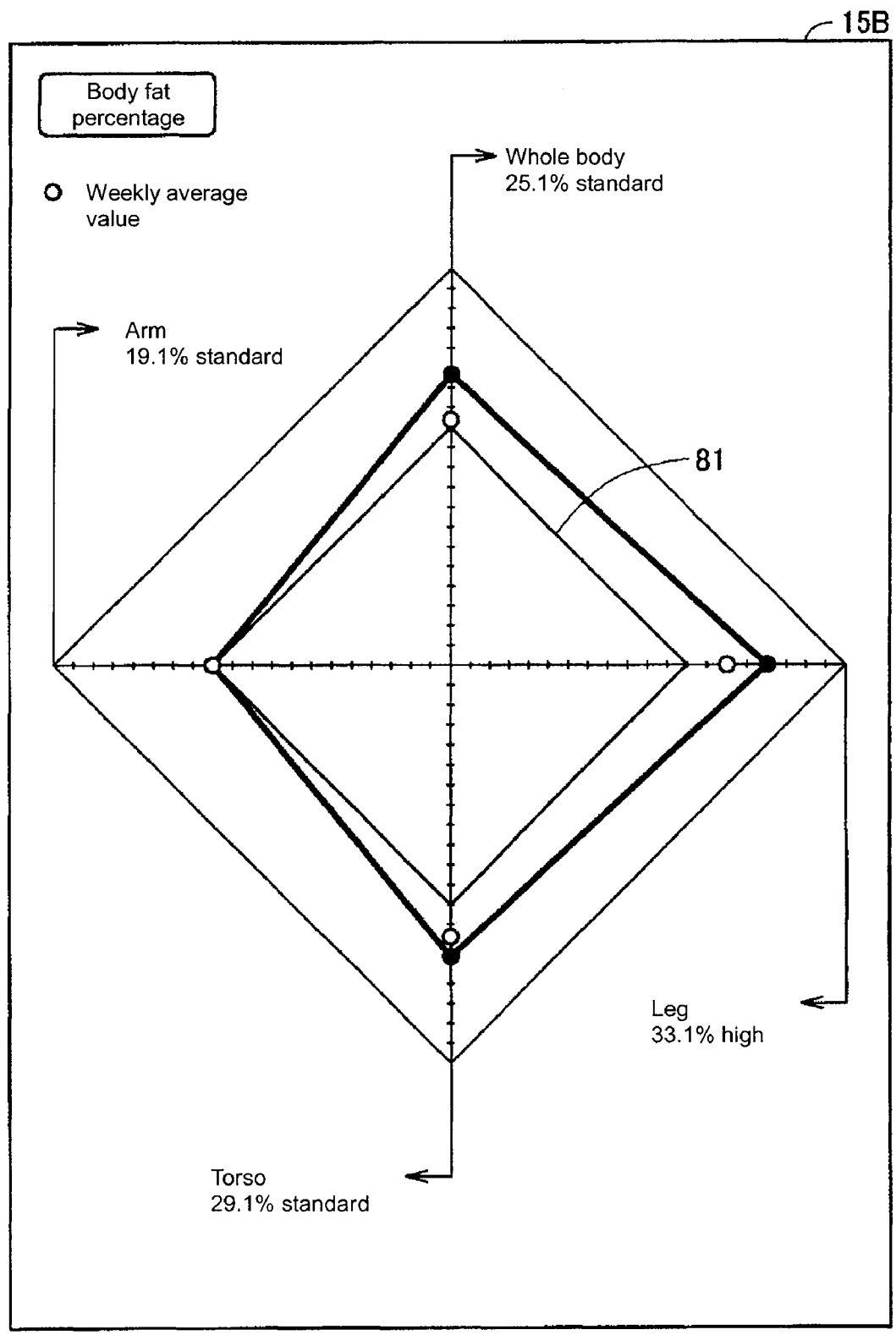
FIG. 20 is a view showing a variant of a graph.

In each embodiment described above, the predetermined graph has been described as a bar graph, but is not limited to a bar graph as long as the position of the body composition for this time and the position of the reference value can be displayed. For instance, it may be a radar chart graph as shown in FIG. 20. Also in such radar chart graph, effects as in each embodiment can be obtained by displaying a line 81 indicating the position of the reference value at a predetermined fixed position.

The body composition display method executed by the body composition measuring instrument of the present invention may be provided as a program. Such program may be recorded on an optical medium such as CD-ROM (Compact Disc-ROM), or a computer readable recording medium such as memory card, and provided as a program product. The program can be provided by downloading via network.

The program product to be provided is executed while being installed in a program storage unit such as flash memory. The program product includes the program itself, and the recording medium recorded with the program.

The embodiments disclosed herein are merely illustrative in all aspects and should not be construed as being restrictive. The scope of the invention is defined by the appended claims rather than the description described above, and all changes that fall within meets and bounds of the claims, or equivalence of such meets and bounds are therefore intended to be embraced by the claims.

The invention claimed is:

1. A body composition measuring instrument comprising:
a plurality of electrodes configured to be contacted to a surface of a body of a user;
a first calculating unit for calculating a body composition of the user by using the electrodes;
a storage section for storing information of a reference value related to a past body composition of the user;
a display control unit determining a position of a body composition calculated for a measurement time during which a current body composition of the user is measured and a position of the reference value calculated by the first calculating unit on a predetermined graph; and
a display section providing a display corresponding to an output from the display control unit; wherein
the position of the reference value is a predetermined fixed position in the predetermined graph;
the reference value corresponds to a body composition calculated by the first calculating unit at a specific time point in the past;
the display control unit includes:
a first determining unit for determining a display mode of a component in the predetermined graph corresponding to the body composition for this time based on the body composition for this time and the reference value,
a second determining unit for determining a range of values of the body composition displayable on the predetermined graph based on the reference value; and
the first determining unit determines the display mode based on the range determined by the second determining unit.

2. The body composition measuring instrument according to claim 1, wherein the predetermined graph includes a first block group and a second block group respectively arranged before and after the position of the reference value.

3. The body composition measuring instrument according to claim 2, wherein number of blocks included in the first block group is greater than number of blocks included in the second block group.

4. The body composition measuring instrument according to claim 1, further comprising:
an operating section accepting an instruction from the user; and
a storage processing unit performing a process of storing the information of the reference value in the storage section; wherein
the storage processing unit includes a first updating unit for updating the reference value when a predetermined instruction is input from the user.

5. The body composition measuring instrument according to claim 4, wherein the first updating unit updates the reference value to the body composition for the measurement time when the predetermined instruction is input in a measurement of the body composition for the measurement time.

6. The body composition measuring instrument according to claim 4, further comprising:
a timer for timing date and time; wherein the body composition calculated by the first calculating unit is stored in correspondence to a measurement date and time for every measurement in the storage section;
a second calculating unit for calculating an average value of the body composition corresponded to the measurement date and time within a predetermined first period and the body composition for this time in the storage section is further provided;
wherein the storage processing unit includes a determining unit for determining whether or not the information of the reference value is stored in the storage section, and
a setting unit for setting the average value as the reference value when determined that the information of the reference value is not stored in the storage section and the body composition for the first period is stored in the storage section.

7. The body composition measuring instrument according to claim 6, wherein the display control unit further displays a position of the average value on the predetermined graph.

8. The body composition measuring instrument according to claim 4, wherein
the information of the reference value includes information on a set date of the reference value; and
a notifying section for notifying to update the reference value when a predetermined second period has elapsed from the set date is further provided.

9. The body composition measuring instrument according to claim 4, wherein the storage processing unit further includes a second updating unit for updating the reference value to the body composition for this time when the body composition for this time reaches an upper limit or a lower limit of a range displayable on the predetermined graph.

10. The body composition measuring instrument according to claim 4, further comprising a notifying section for notifying the first calculating unit to update the reference value when the body composition for this time approaches an upper limit or a lower limit of a range displayable on the predetermined graph.

11. The body composition measuring instrument according to claim 1, wherein the display control unit further determines a comparison result of the body composition for this time and a predetermined standard value in an attribute of the user near the predetermined graph to be displayed on the display unit.

12. The body composition measuring instrument according to claim 1, further comprising a target value storage section for storing a target value input by the user; wherein
the display control unit includes a selecting unit for selecting one of a first mark and a second mark predefined based on whether or not the body composition for this time has approached that target value than before; and
the mark selected by the selecting unit is further displayed with the predetermined graph.

13. The body composition measuring instrument according to claim 1, wherein
the display control unit includes a selecting unit for selecting one of a first mark and a second mark predefined based on whether or not the body composition for the measurement time has changed in a desired tendency from a prior body composition of the user; and
the mark selected by the selecting unit is further displayed with the predetermined graph.

* * * * *